(12) United States Patent
Fawzy et al.

(10) Patent No.: US 10,314,821 B2
(45) Date of Patent: Jun. 11, 2019

(54) CRYSTALLINE FORMS OF 4-CYANO-N-(2-(4,4-DIMETHYLCYCLOHEX-1-EN-1-YL)-6-(2,2,6,6-TETRAMETHYLTETRAHYDRO-2H-PYRAN-4-YL)PYRIDIN-3-YL)-1H-IMIDAZOLE-2-CARBOXAMIDE

(71) Applicant: Janssen Pharmaceutica NV, Beerse (BE)

(72) Inventors: Nagy E. Fawzy, Piscataway, NJ (US); David Breslin, Telford, PA (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 15/651,385

(22) Filed: Jul. 17, 2017

(65) Prior Publication Data

US 2018/0133197 A1    May 17, 2018

Related U.S. Application Data

(60) Provisional application No. 62/363,622, filed on Jul. 18, 2016.

(51) Int. Cl.
| | | |
|---|---|---|
| A61K 31/4178 | (2006.01) | |
| C07D 405/14 | (2006.01) | |
| A61P 5/48 | (2006.01) | |
| A61P 19/02 | (2006.01) | |
| A61P 31/18 | (2006.01) | |
| A61P 35/00 | (2006.01) | |
| A61K 31/167 | (2006.01) | |
| A61K 31/351 | (2006.01) | |
| A61K 31/44 | (2006.01) | |

(52) U.S. Cl.
CPC ........ *A61K 31/4178* (2013.01); *A61K 31/167* (2013.01); *A61K 31/351* (2013.01); *A61K 31/44* (2013.01); *A61P 5/48* (2018.01); *A61P 19/02* (2018.01); *A61P 31/18* (2018.01); *A61P 35/00* (2018.01); *C07D 405/14* (2013.01)

(58) Field of Classification Search
None
See application file for complete search history.

(56) References Cited

U.S. PATENT DOCUMENTS

| | | |
|---|---|---|
| 8,497,376 B2 | 7/2013 | Illig et al. |
| 2014/0045789 A1 | 2/2014 | Kolodziejczyk et al. |
| 2016/0015700 A1 | 1/2016 | De Boer et al. |

*Primary Examiner* — Samantha L Shterengarts
(74) *Attorney, Agent, or Firm* — BakerHostetler LLP

(57) ABSTRACT

The present disclosure discusses crystalline forms of 4-cyano-N-[2-(4,4-dimethylcyclohex-1-en-1-yl)-6-(2,2,6,6-tetramethyltetrahydro-2H-pyran-4-yl)pyridine-3-yl]-1H-imidazole-2-carboxamide.

41 Claims, 18 Drawing Sheets

XRPD pattern of Compound A, Form IIA

XRPD pattern of Compound A, Form III

XRPD pattern of Compound A, Form IV

XRPD pattern of Compound A, Form V

XRPD pattern of Compound A, Form VI

DSC thermograms of Compound A, Form I-V

XRPD pattern of Compound A, Form I, prepared by slurrying the HCl salt of Compound A with water DSC thermogram of Compound A, Form I, prepared by slurrying the HCl salt of Compound A with water TGA spectrum of Compound A, Form I, prepared by slurrying the HCl salt of Compound A with water DSC thermogram of the HCl salt of Compound A TGA spectrum of the HCl salt of Compound A DVS spectrum of the HCl salt of Compound A, showing two cycles of adsorption/desorption

CRYSTALLINE FORMS OF 4-CYANO-N-(2-(4,4-DIMETHYLCYCLOHEX-1-EN-1-YL)-6-(2,2,6,6-TETRAMETHYLTETRAHYDRO-2H-PYRAN-4-YL)PYRIDIN-3-YL)-1H-IMIDAZOLE-2-CARBOXAMIDE

This application claims priority to U.S. Provisional Patent Application No. 62/363,622, filed Jul. 18, 2016, the entire disclosure of which is hereby incorporated in its entirety.

TECHNICAL FIELD

The present inventions are directed to crystalline forms of 4-cyano-N-(2-(4,4-dimethylcyclohex-1-en-1-yl)-6-(2,2,6,6-tetramethyltetrahydro-2H-pyran-4-yl)pyridin-3-yl)-1H-imidazole-2-carboxamide.

BACKGROUND

Protein kinases are enzymes that serve as key components of signal transduction pathways by catalyzing the transfer of the terminal phosphate from adenosine 5'-triphosphate (ATP) to the hydroxy group of tyrosine, serine and threonine residues of proteins. As a consequence, protein kinase inhibitors and substrates are valuable tools for assessing the physiological consequences of protein kinase activation. The overexpression or inappropriate expression of normal or mutant protein kinases in mammals has been demonstrated to play significant roles in the development of many diseases, including cancer and diabetes.

Protein kinases can be divided into two classes: those which preferentially phosphorylate tyrosine residues (protein tyrosine kinases) and those which preferentially phosphorylate serine and/or threonine residues (protein serine/threonine kinases). Protein tyrosine kinases perform diverse functions ranging from stimulation of cell growth and differentiation to arrest of cell proliferation. They can be classified as either receptor protein tyrosine kinases or intracellular protein tyrosine kinases. The receptor protein tyrosine kinases, which possess an extracellular ligand binding domain and an intracellular catalytic domain with intrinsic tyrosine kinase activity, are distributed among 20 subfamilies.

Feline McDonough Sarcoma (FMS) is the receptor-tyrosine kinase responsible for cellular response to colony stimulating factor-1 (CSF-1). CSF-1 is the primary growth factor for the macrophage/osteoclast lineage. Inhibitors of FMS kinase reduce macrophage survival in tissues and osteoclastogenesis in bone. Accordingly, diabetes, angiogenesis, psoriasis, restenosis, ocular diseases, schizophrenia, rheumatoid arthritis, cardiovascular disease and cancer are exemplary of pathogenic conditions that have been linked with abnormal protein tyrosine kinase activity.

4-Cyano-N-[2-(4,4-dimethylcyclohex-1-en-1-yl)-6-(2,2,6,6-tetramethyltetrahydro-2H-pyran-4-yl)pyridine-3-yl]-1H-imidazole-2-carboxamide exhibits an inhibitory activity against FMS to treat diseases where macrophages and osteoclasts are pathogenic, namely rheumatoid arthritis and cancer metastasis to bone.

There remains a need to provide alternate forms of 4-cyano-N-[2-(4,4-dimethylcyclohex-1-en-1-yl)-6-(2,2,6,6-tetramethyltetrahydro-2H-pyran-4-yl)pyridine-3-yl]-1H-imidazole-2-carboxamide.

SUMMARY

The present disclosure provides crystalline forms of 4-cyano-N-[2-(4,4-dimethylcyclohex-1-en-1-yl)-6-(2,2,6,6-tetramethyltetrahydro-2H-pyran-4-yl)pyridine-3-yl]-1H-imidazole-2-carboxamide. Pharmaceutical compositions comprising these crystalline forms and methods of using these crystalline forms for inhibiting colony-stimulating factor-1 receptor are also described.

BRIEF DESCRIPTION OF THE DRAWINGS

The summary, as well as the following detailed description, is further understood when read in conjunction with the appended drawings. For the purpose of illustrating the invention, there are shown in the drawings exemplary embodiments of the invention; however, the invention is not limited to the specific methods, compositions, and devices disclosed. In addition, the drawings are not necessarily drawn to scale. In the drawings.

DETAILED DESCRIPTION OF ILLUSTRATIVE EMBODIMENTS

Figure 1:
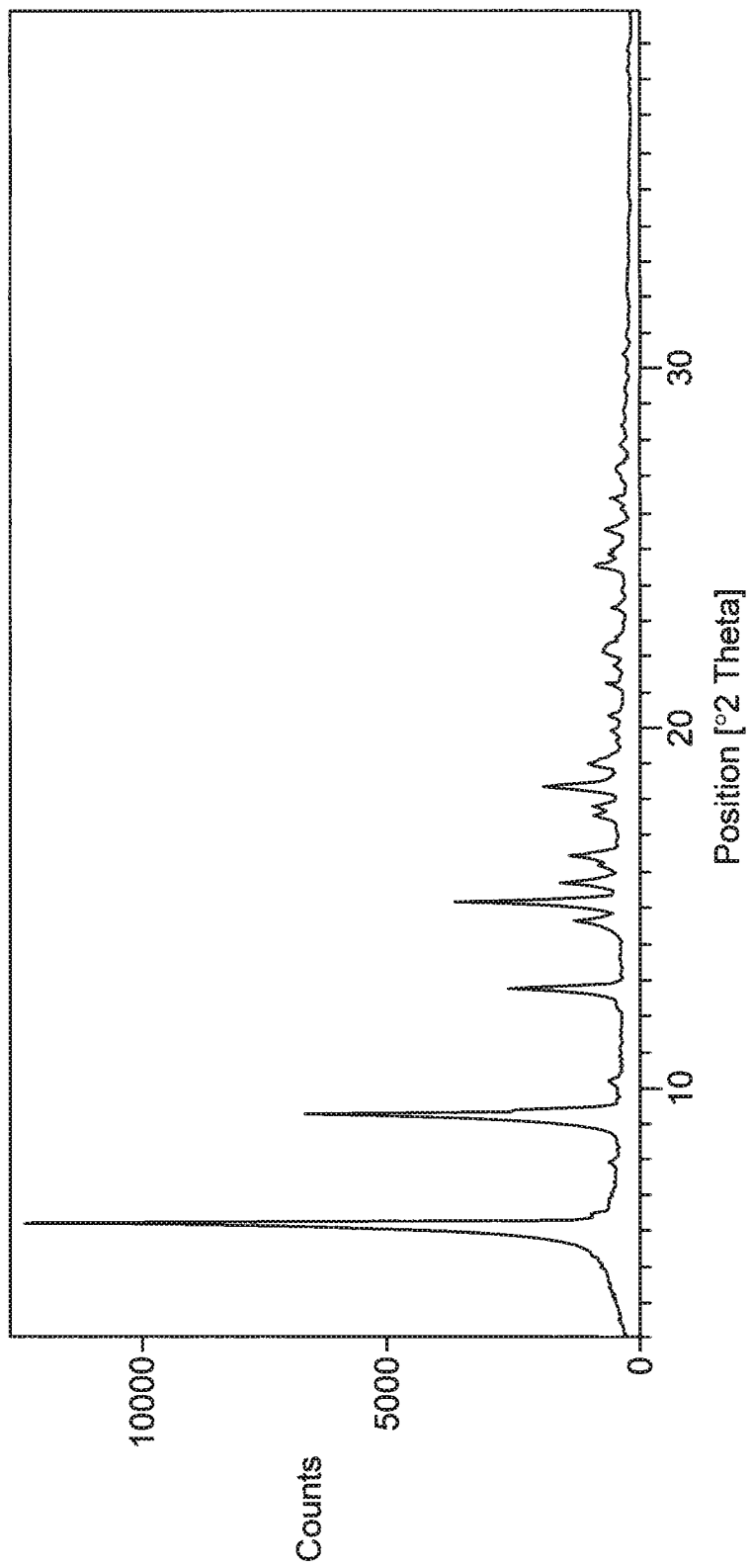
FIG. 1 is an X-ray powder diffraction (XRPD) pattern of Compound A, Form I.

The disclosure may be more fully appreciated by reference to the following description, including the following glossary of terms and the concluding examples. It is to be appreciated that certain features of the disclosed compositions and methods which are, for clarity, described herein in the context of separate aspects, may also be provided in combination in a single aspect. Conversely, various features of the disclosed compositions and methods that are, for brevity, described in the context of a single aspect, may also be provided separately or in any subcombination.

The terms "form" and "polymorph" are interchangeable and refer to solid state crystalline forms of Compound A. Forms I, II, IIA, IIB, III, IV, V, and VI are each distinct crystalline forms of polymorphs.

The term "subject" includes humans. The terms "human," "patient," and "subject" are used interchangeably herein.

"Treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder.

Some of the quantitative expressions given herein are not qualified with the term "about." It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

"Pharmaceutically acceptable" means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

"Pharmaceutically acceptable vehicle" refers to a diluent, adjuvant, excipient or carrier with which a compound of the disclosure is administered. A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of an agent and that is compatible therewith. Examples of excipients include calcium carbonate, calcium phosphate, various sugars and types of starch, cellulose derivatives, gelatin, vegetable oils, and polyethylene glycols.

Further, some of the quantitative expressions herein are recited as a range from about amount X to about amount Y. It is understood that wherein a range is recited, the range is not limited to the recited upper and lower bounds, but rather includes the full range from about amount X through about amount Y, or any amount or range therein.

Described herein are novel crystalline forms of 4-cyano-N-[2-(4,4-dimethylcyclohex-1-en-1-yl)-6-(2,2,6,6-tetramethyltetrahydro-2H-pyran-4-yl)pyridin-3-yl]-1H-imidazole-2-carboxamide, which has the following structure and is identified herein as "Compound A." In some embodiments, Compound A is a free base.

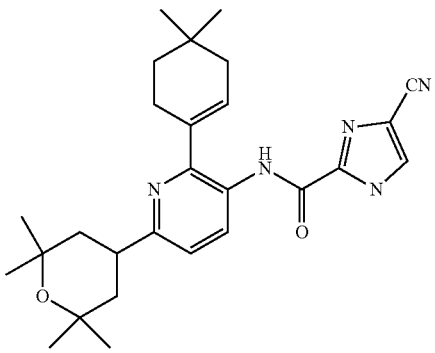

Compound A

In the development of pharmaceuticals, in particular, orally delivered drugs, it is often advantageous to have novel crystalline forms of such drugs that possess improved physical properties, for example, increased aqueous solubility and stability. The crystalline forms of Compound A described herein possess improved properties over those solid forms of Compound A previously described.

Compound A (as a free base) and Compound A, as its corresponding hydrochloride salt may be prepared, for example, as described in U.S. Pat. No, 8,497,376 and US Patent Publication Nos. 2014/0045789 and 2016/0015700, which are incorporated herein by reference, as well as using the procedures described in Example 1. In some embodiments, Compound A is prepared from its hydrochloride salt. In other embodiments, Compound A is prepared from its hydrochloride salt as described in Example 1.

Figure 9:
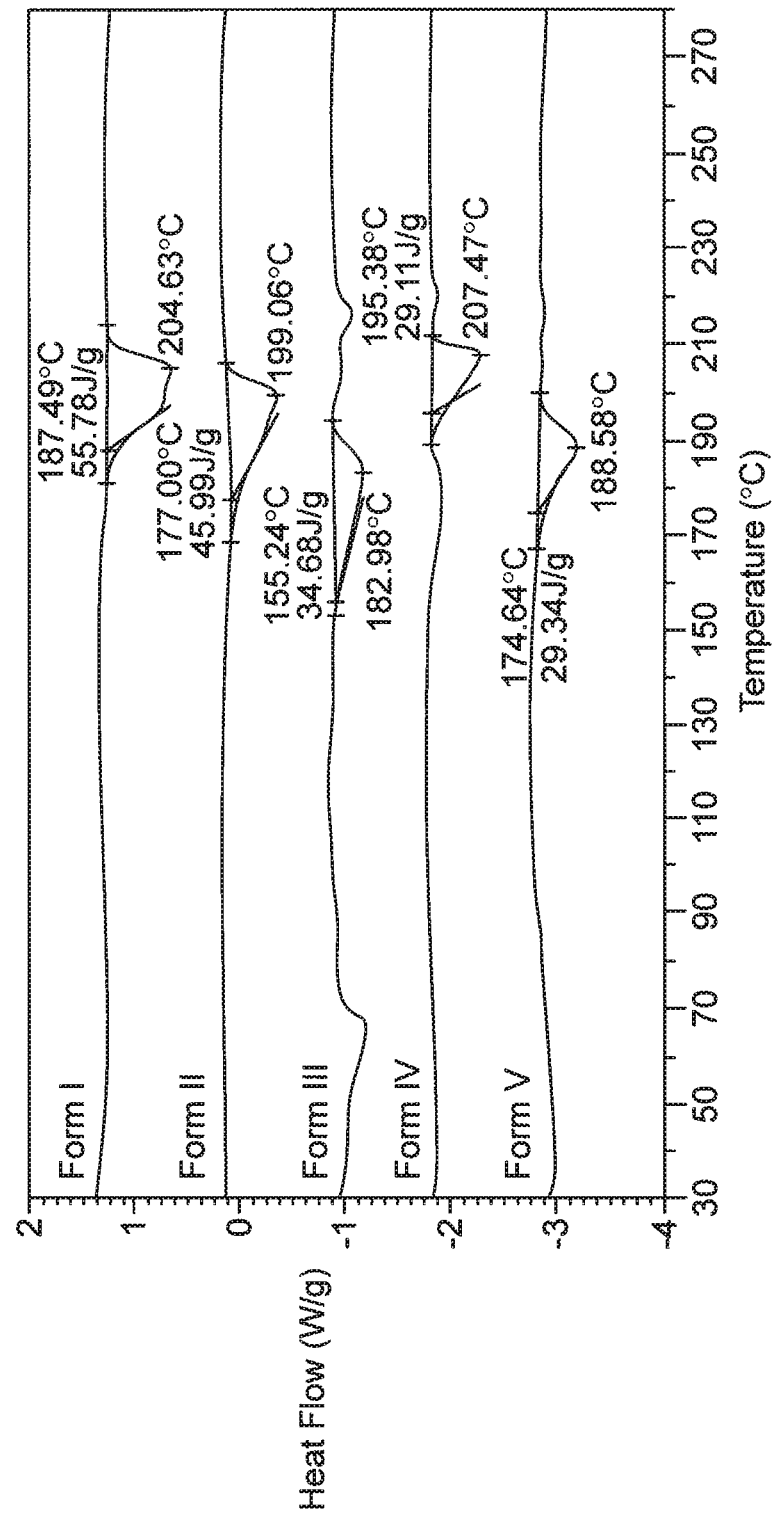
FIG. 9 is a differential scanning calorimetry (DSC) thermogram for Compound A, Form I, Form II, Form III, Form IV, and Form V.
Figure 10:
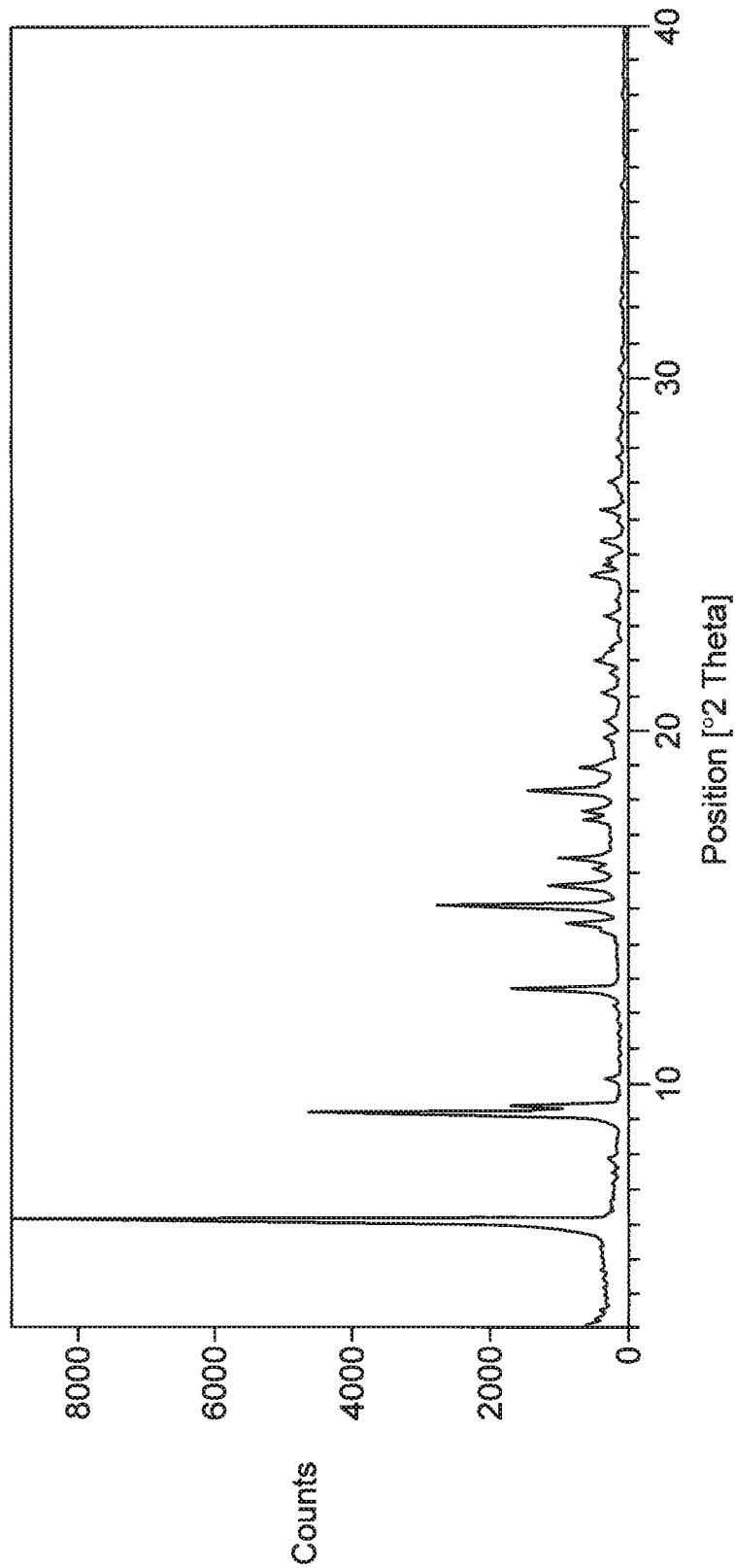
FIG. 10 is an XRPD pattern for Compound A, Form I, prepared by slurrying the HCl salt of Compound A with water.
Figure 11:
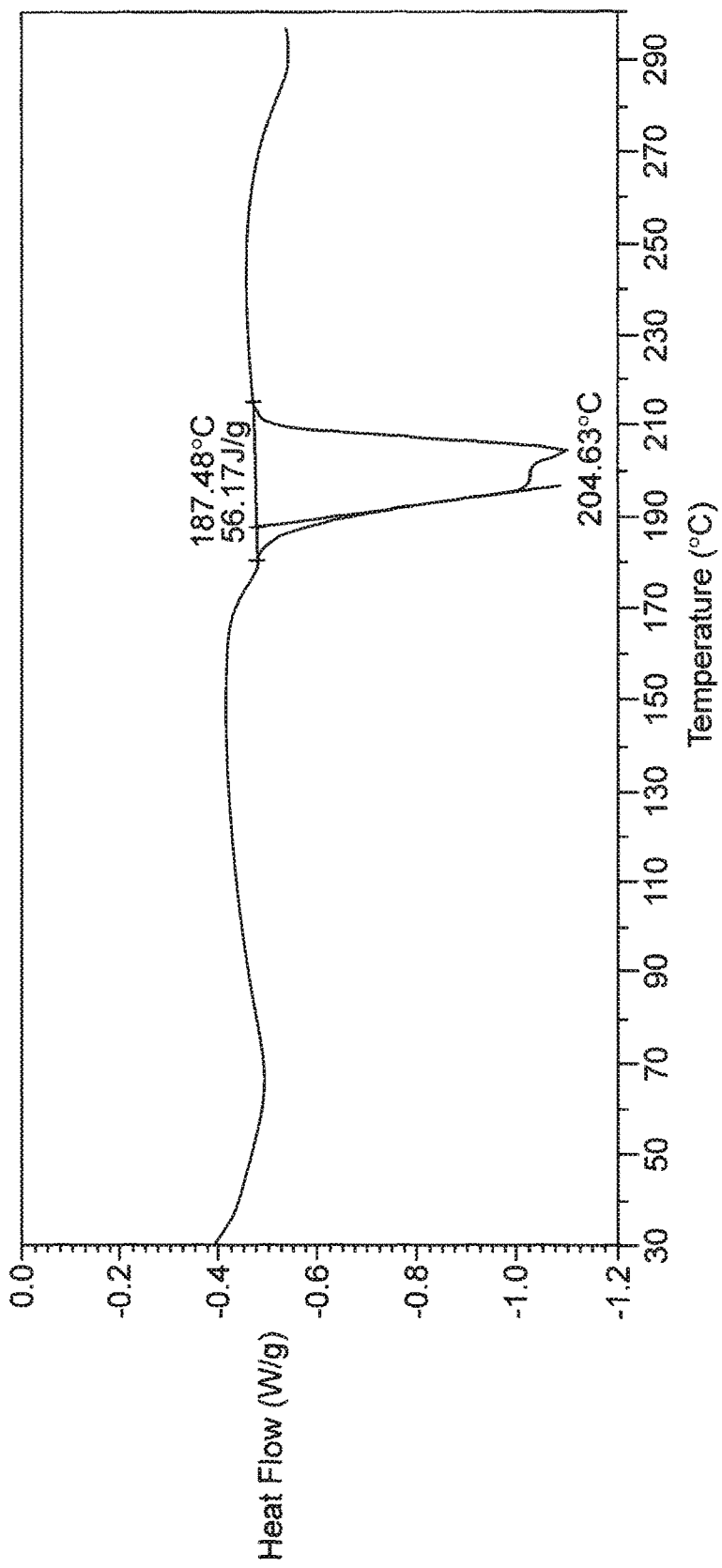
FIG. 11 is a DSC thermogram of Compound A, Form I, prepared by slurrying the HCl salt of Compound A with water.

Various crystalline forms of Compound A are described and characterized herein. The crystalline forms described herein include Forms I, II, IIA, IIB, III, IV, V, and VI. In some embodiments, crystalline Compound A, Form I is provided. Compound A, Form I produces an X-ray powder diffraction pattern comprising peaks at 6.1, 9.2, 9.4, 12.7, 15.1, 15.7, and 18.4 degrees two theta±0.2 degrees two theta. The X-ray powder diffraction pattern may further comprise one or more peaks at 14.6, 16.4, or 19.0 degrees two theta±0.2 degrees two theta. Compound A, Form I, may also be characterized by a differential scanning calorimetry thermogram comprising an onset temperature at 187.5° C. and/or an endotherm with a peak temperature at 204.6° C. Compound A, Form I may further be characterized by an X-ray powder diffraction pattern substantially as depicted in FIG. 1 or FIG. 10 and/or a differential scanning calorimetry thermogram substantially as depicted in FIG. 9 or FIG. 11. Compound A, Form I may further be characterized by an X-ray powder diffraction pattern having four, five, six, seven, eight, nine or more peaks selected from those peaks identified in Table 3A. Compound A, Form I may further be characterized by an X-ray powder diffraction pattern comprising those peaks identified in Table 3A, wherein the relative intensity of the peaks is greater than about 2%, preferably greater than about 5%, more preferably greater than about 10%, more preferably greater than about 15%.

Figure 2:
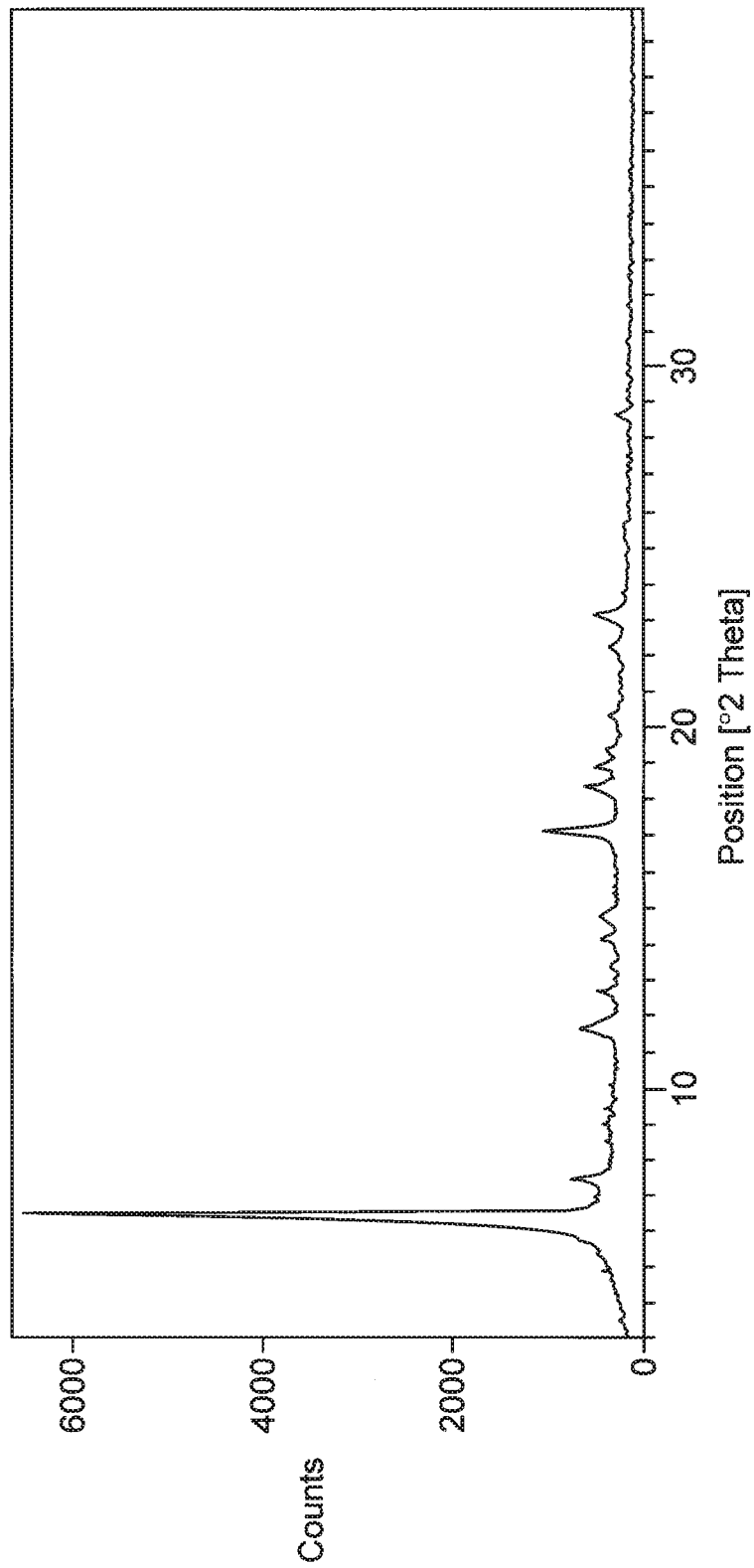
FIG. 2 is an XRPD pattern of Compound A, Form II.

In other embodiments, Compound A, Form II, is provided. Compound A, Form II produces an X-ray powder diffraction pattern comprising peaks at 6.3, 7.3, 11.5, 17.0, and 18.3 degrees two theta±0.2 degrees two theta. The X-ray powder diffraction pattern for Compound A, Form II may further comprise one or more peaks at 14.0, 14.6, 18.8, or 23.0 degrees two theta±0.2 degrees two theta. Compound A, Form II further may be characterized by a differential scanning calorimetry thermogram comprising an onset temperature at about 177.0° C. and/or an endotherm with a peak temperature at about 199.1° C. Compound A, Form II also may be characterized by an X-ray powder diffraction pattern substantially as depicted in FIG. 2 and/or a differential scanning calorimetry thermogram substantially as depicted in FIG. 9. Compound A, Form II may further be characterized by an X-ray powder diffraction pattern having four, five, six, seven, eight, nine or more peaks selected from those peaks identified in Table 3B. Compound A, Form II may further be characterized by an X-ray powder diffraction pattern comprising those peaks identified in Table 3A, wherein the relative intensity of the peaks is greater than about 2%, preferably greater than about 5%, more preferably greater than about 10%.

Figure 3:
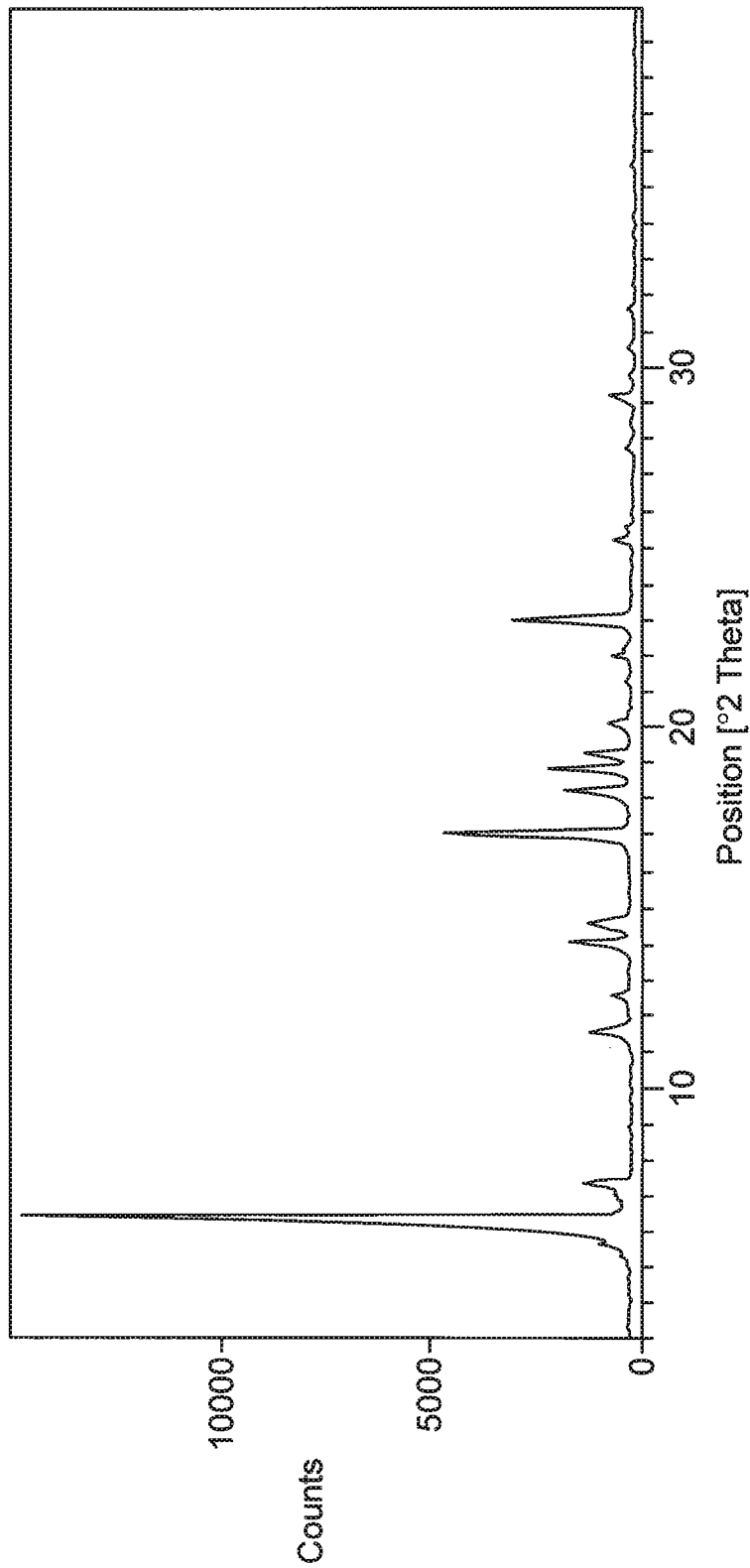
FIG. 3 is an XRPD pattern of Compound A, Form IIA.

In further embodiments, Compound A, Form IIA is provided. Compound A, Form IIA produces an X-ray powder diffraction pattern comprising peaks at 6.4, 14.1, 14.6, 17.1, 18.3, 18.9, 19.3 and 23.0 degrees two theta±0.2 degrees two theta. The X-ray powder diffraction pattern may further comprise one or more peaks at 5.9, 7.3, 7.4, 11.5, 12.6, 18.3, 18.9, 20.2, 25.3, or 29.3 degrees two theta±0.2 degrees two theta. Compound A, Form IIA may also be characterized by an X-ray powder diffraction pattern substantially as depicted in FIG. 3. Compound A, Form IIA may further be characterized by an X-ray powder diffraction pattern having four, five, six, seven, eight, nine or more peaks selected from those peaks identified in Table 3C. Compound A, Form IIA may further be characterized by an X-ray powder diffraction pattern comprising those peaks identified in Table 3A, wherein the relative intensity of the peaks is greater than about 2%, preferably greater than about 5%, more preferably greater than about 10%.

Figure 4:
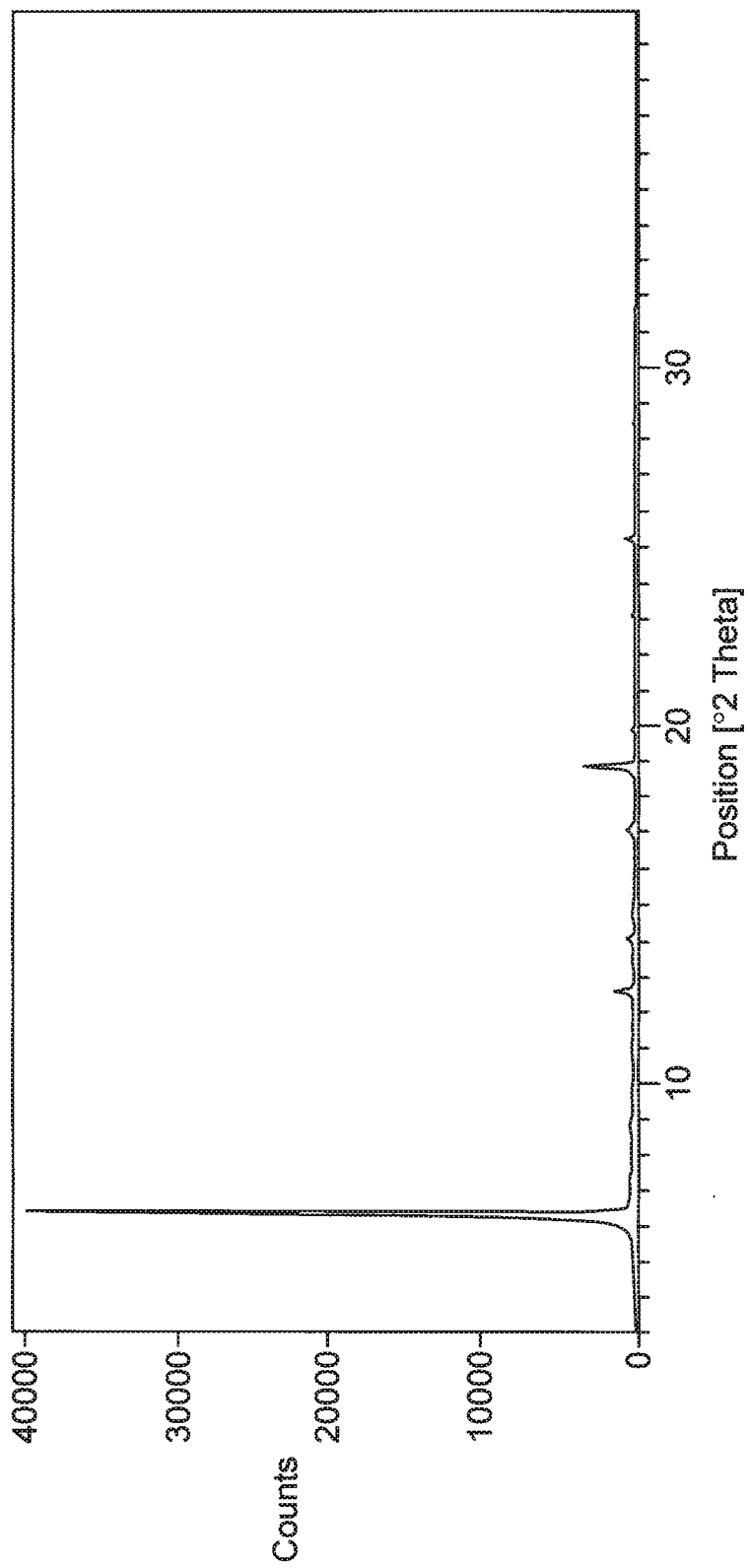
FIG. 4 is an XRPD pattern of Compound A, Form IIB.

In other embodiments, Compound A, Form IIB is provided. Compound A, Form IIB produces an X-ray powder diffraction pattern comprising peaks at 6.3 and 18.9 degrees two theta±0.2 degrees two theta. The X-ray powder diffraction pattern may further comprise one or more peaks at 12.6, 14.0 or 25.2 degrees two theta±0.2 degrees two theta. Compound A, Form IIB may also be characterized by an X-ray powder diffraction pattern substantially as depicted in FIG. 4. Compound A, Form IIB may further be characterized by an X-ray powder diffraction pattern having four, five, six, seven, eight, nine or more peaks selected from those peaks identified in Table 3D. Compound A, Form IIB may further be characterized by an X-ray powder diffraction pattern comprising those peaks identified in Table 3A, wherein the relative intensity of the peaks is greater than about 2%, preferably greater than about 5%, more preferably greater than about 10%.

Figure 5:
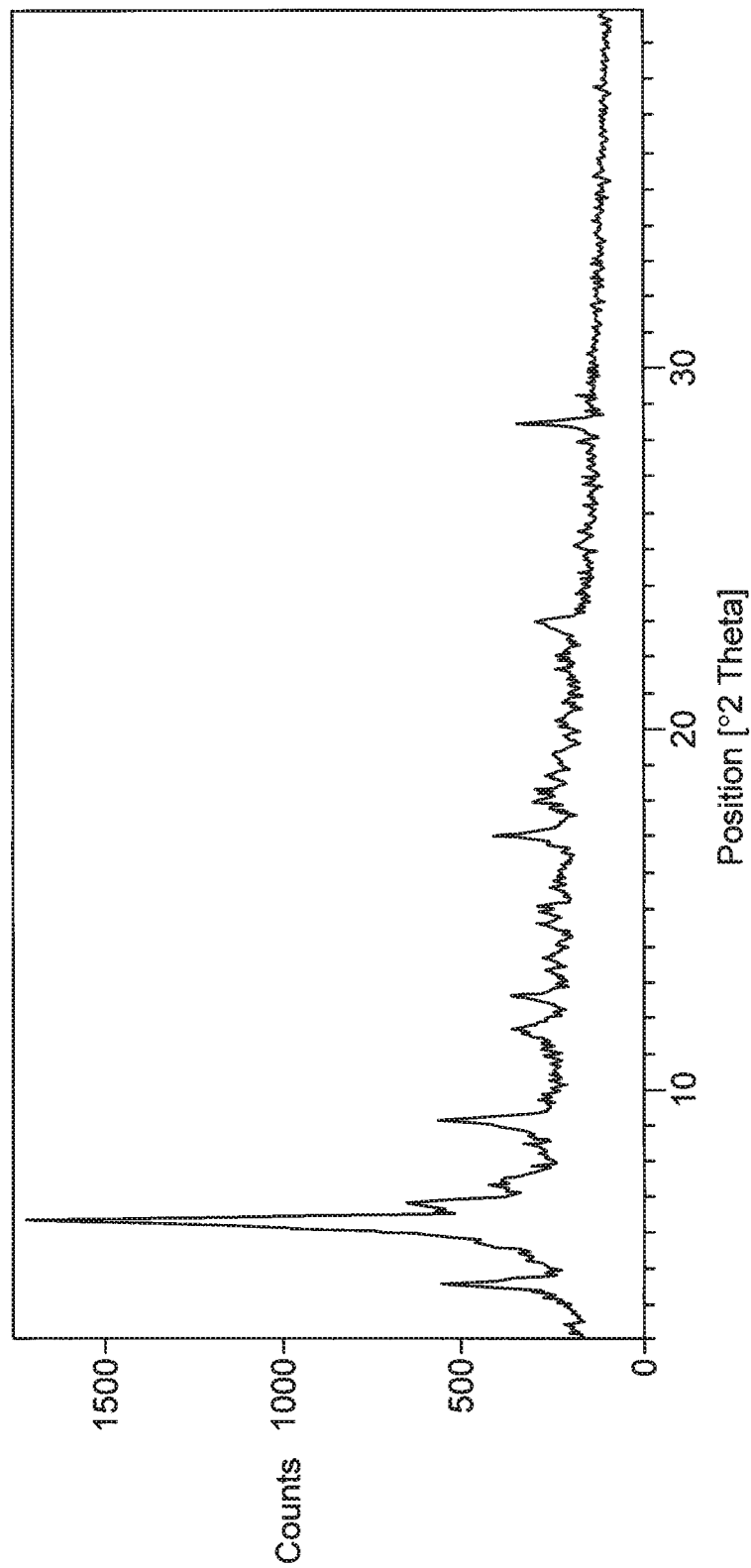
FIG. 5 is an XRPD pattern of Compound A, Form III.

In still further embodiments, Compound A, Form III is provided. Compound A, Form III produces an X-ray powder diffraction pattern comprising peaks at 4.6, 6.3, 6.8, 9.1, 17.1, and 28.5 degrees two theta±0.2 degrees two theta. The X-ray powder diffraction pattern may further comprise one or more peaks at 7.4, 11.7, 12.6, 18.1 or 23.0 degrees two theta±0.2 degrees two theta. Compound A, Form III also may be characterized by a differential scanning calorimetry thermogram comprising an onset temperature at about 155.4° C. and/or an endotherm with a peak temperature at about 182.9° C. Compound A, Form III further may be characterized by an X-ray powder diffraction pattern substantially as depicted in FIG. 5 and/or a differential scanning calorimetry thermogram substantially as depicted in FIG. 9. Compound A, Form III may further be characterized by an X-ray powder diffraction pattern having four, five, six, seven, eight, nine or more peaks selected from those peaks identified in Table 3E. Compound A, Form III may further be characterized by an X-ray powder diffraction pattern comprising those peaks identified in Table 3A, wherein the relative intensity of the peaks is greater than about 5%, preferably greater than about 10%, more preferably greater than about 15%.

Figure 6:
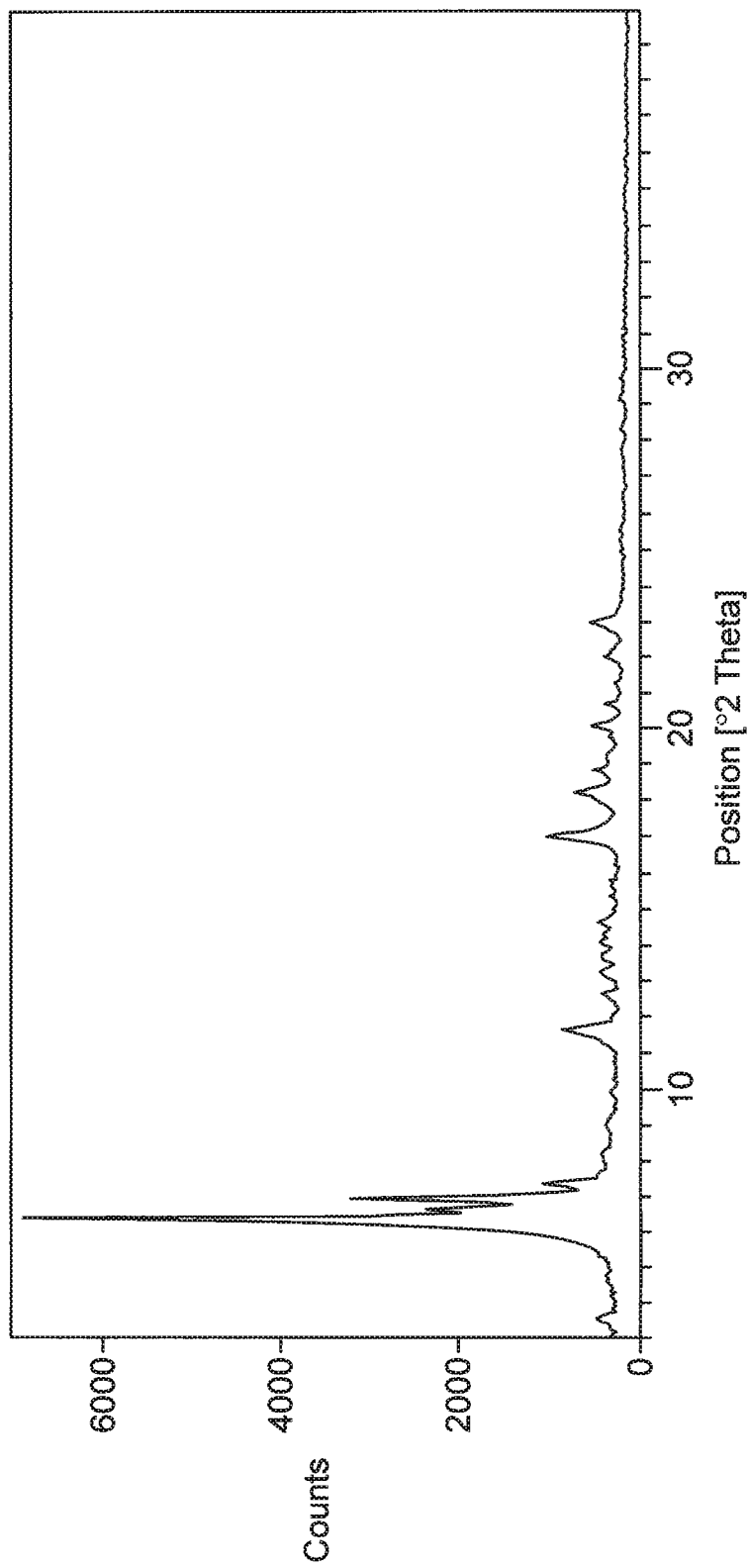
FIG. 6 is an XRPD pattern of Compound A, Form IV.

In yet other embodiments, Compound A, Form IV is provided. Compound A, Form IV produces an X-ray powder diffraction pattern comprising peaks at 6.3, 6.6, 6.9, 7.3, 11.7, 17.1 and 18.3 degrees two theta±0.2 degrees two theta. The X-ray powder diffraction pattern further may comprise one or more peaks at 3.5, 14.6, 18.9, 20.2 or 23.0 degrees two theta±0.2 degrees two theta. Compound A, Form IV may be further characterized by a differential scanning calorimetry thermogram comprising an onset temperature at about 195.4° C. and/or an endotherm with a peak temperature at about 207.5° C. Compound A, Form IV also may be characterized by an X-ray powder diffraction pattern substantially as depicted in FIG. 6 and/or a differential scanning calorimetry thermogram substantially as depicted in FIG. 9. Compound A, Form IV may further be characterized by an X-ray powder diffraction pattern having four, five, six, seven, eight, nine or more peaks selected from those peaks identified in Table 3F. Compound A, Form IV may further be characterized by an X-ray powder diffraction pattern comprising those peaks identified in Table 3A, wherein the relative intensity of the peaks is greater than about 2%, preferably greater than about 5%, more preferably greater than about 10%

Figure 7:
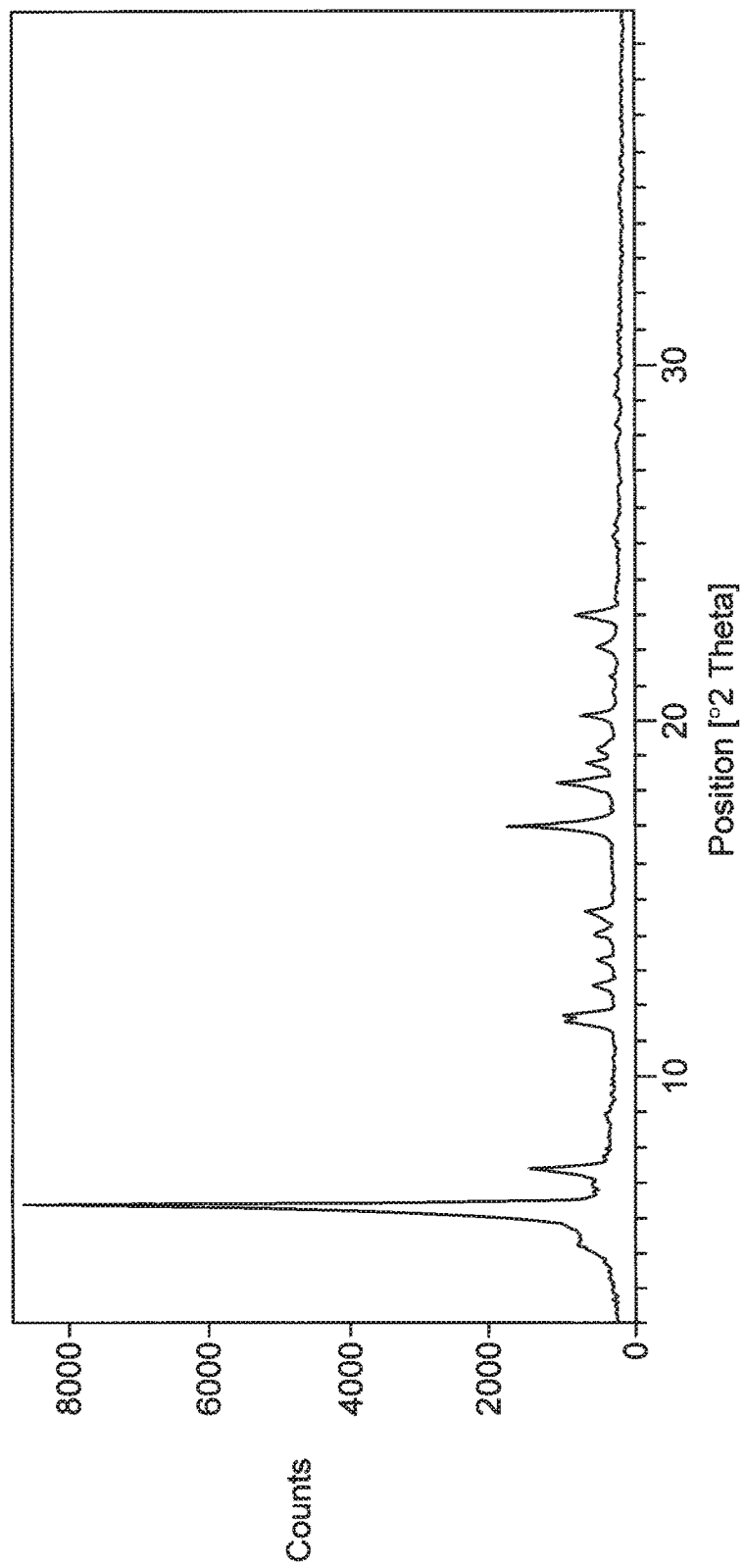
FIG. 7 is an XRPD pattern of Compound A, Form V.

In further embodiments, Compound A, Form V is provided. Compound A, Form V produces an X-ray powder diffraction pattern comprising peaks at 6.3, 7.4, 11.5, 11.7, 17.0, 18.3 and 23.0 degrees two theta±0.2 degrees two theta. The X-ray powder diffraction pattern may further comprise one or more peaks at 5.3, 12.6, 13.3, 14.0, 14.7, 18.3, 19.2, 20.2 or 22.1 degrees two theta±0.2 degrees two theta. Compound A, Form V further may be characterized by a differential scanning calorimetry thermogram comprising an onset temperature at about 174.6° C. and/or an endotherm with a peak temperature at about 188.6° C. Compound A, Form V also may be characterized by an X-ray powder diffraction pattern substantially as depicted in FIG. 7 and/or a differential scanning calorimetry thermogram substantially as depicted in FIG. 9. Compound A, Form V may further be characterized by an X-ray powder diffraction pattern having four, five, six, seven, eight, nine or more peaks selected from those peaks identified in Table 3G. Compound A, Form V may further be characterized by an X-ray powder diffraction pattern comprising those peaks identified in Table 3A, wherein the relative intensity of the peaks is greater than about 2%, preferably greater than about 5%, more preferably greater than about 10%

Figure 8:
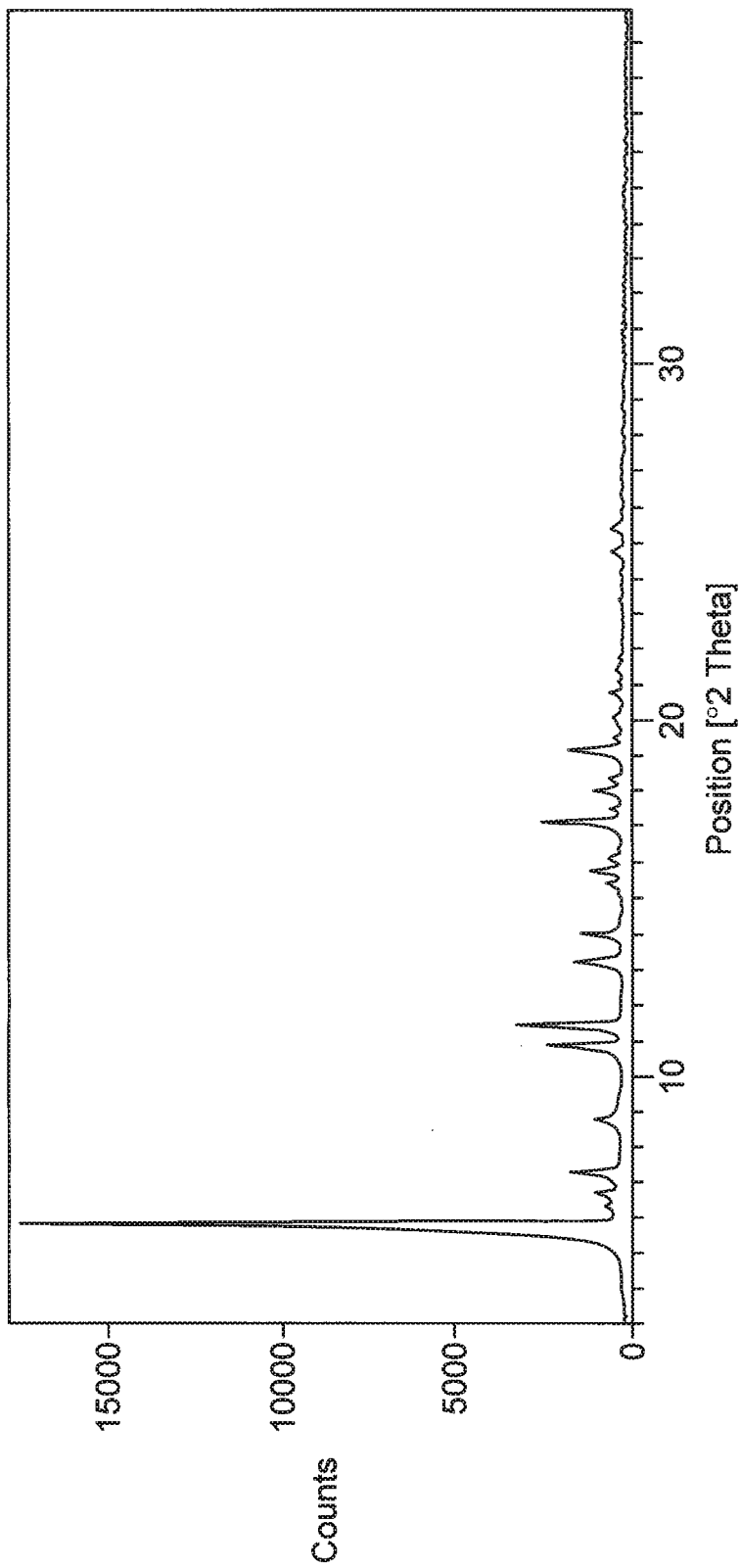
FIG. 8 is an XRPD pattern of Compound A, Form VI.

In yet other embodiments, Compound A, Form VI is provided. Compound A, Form VI produces an X-ray powder diffraction pattern comprising peaks at 5.7, 10.8, 11.4 and 17.1 degrees two theta±0.2 degrees two theta. The X-ray powder diffraction pattern may further comprise one or more peaks at 7.3, 13.2, 14.0, 15.7, 18.0 or 19.2 degrees two theta±0.2 degrees two theta. Compound A, Form VI also may be characterized by an X-ray powder diffraction pattern substantially as depicted in FIG. 8. Compound A, Form VI may further be characterized by an X-ray powder diffraction pattern having four, five, six, seven, eight, nine or more peaks selected from those peaks identified in Table 3H. Compound A, Form VI may further be characterized by an X-ray powder diffraction pattern comprising those peaks identified in Table 3A, wherein the relative intensity of the peaks is greater than about 2%, preferably greater than about 5%, more preferably greater than about 10%.

In treatment methods according to the disclosure, an effective amount of a pharmaceutical agent according to the disclosure is administered to a subject suffering from or diagnosed as having such a disease, disorder, or condition. An "effective amount" means an amount or dose sufficient to generally bring about the desired therapeutic benefit in patients in need of such treatment for the designated disease, disorder, or condition. Effective amounts or doses of the compounds of the present disclosure may be ascertained by routine methods such as modeling, dose escalation studies or clinical trials, and by taking into consideration routine factors, e.g., the mode or route of administration or drug delivery, the pharmacokinetics of the compound, the severity and course of the disease, disorder, or condition, the subject's previous or ongoing therapy, the subject's health status and response to drugs, and the judgment of the treating physician. An example of a dose is in the range of from about 0.001 to about 200 mg of compound per kg of subject's body weight per day, preferably about 0.05 to 100 mg/kg/day, or about 1 to 35 mg/kg/day, in single or divided dosage units (e.g., BID, TID, QID). For a 70-kg human, an illustrative range for a suitable dosage amount is from about 0.05 to about 7 g/day, or about 0.2 to about 2.5 g/day.

In addition, the compounds may be used in combination with additional active ingredients in the treatment of the above conditions. The additional active ingredients may be co-administered separately with a compound of the disclosure or included in a pharmaceutical composition according to the disclosure. The combination may serve to increase efficacy (e.g., by including in the combination a compound potentiating the potency or effectiveness of a compound), decrease one or more side effects, or decrease the required dose of the compound.

The compounds are used, alone or in combination with one or more additional active ingredients, to formulate pharmaceutical compositions of the disclosure. A pharmaceutical composition of the disclosure comprises: (a) an effective amount of at least one compound in accordance with the disclosure; and (b) a pharmaceutically acceptable excipient.

Delivery forms of the pharmaceutical compositions containing one or more dosage units of compounds may be prepared using suitable pharmaceutical excipients and compounding techniques known or that become available to those skilled in the art. The compositions may be administered in the inventive methods by a suitable route of delivery, e.g., oral, parenteral, rectal, topical, or ocular routes, or by inhalation. The route of delivery includes immediate release, timed release and sustained release.

The preparation may be in the form of tablets, caplets, gelcaps, capsules, drops, sachets, dragees, powders, granules, lozenges, powders for reconstitution, liquid preparations, or suppositories. In some embodiments, the compositions are formulated for intravenous infusion, topical administration, or oral administration.

For oral administration, the compounds of the disclosure can be provided in the form of tablets or capsules, or as a solution, elixir, emulsion, or suspension. The total daily dosage of about 5 mg to 5 g daily, preferably about 10 mg to about 1000 mg daily, more preferably about 50 mg to about 500 mg daily, may be accomplished by dosing once, twice, three, or four times per day.

Oral tablets may include one or more of a compound according to the disclosure mixed with pharmaceutically acceptable excipients such as inert diluents, disintegrating agents, binding agents, lubricating agents, sweetening agents, flavoring agents, coloring agents, suspending agents, dyes and preservative agents. Suitable inert fillers include sodium and calcium carbonate, sodium and calcium phosphate, lactose, starch, sugar, glucose, methyl cellulose, magnesium stearate, mannitol, sorbitol, and the like. Liquid oral excipients may include ethanol, glycerol, water, and the like. Starch, polyvinyl-pyrrolidone, sodium starch glycolate, microcrystalline cellulose, and alginic acid are suitable disintegrating agents. Binding agents may include starch and gelatin. The lubricating agent, if present, may be magnesium stearate, stearic acid or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, compounds of the disclosure may be mixed with a solid, semisolid, or liquid diluent. Soft gelatin capsules may be prepared by mixing the compound of the disclosure with water, an oil such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions or syrups or may be lyophilized or presented as a dry product for reconstitution with water or other suitable vehicle before use. Such liquid compositions may optionally contain pharmaceutically acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The compounds may also be administered by non-oral routes. For example, the compositions may be formulated for rectal administration as a suppository. For parenteral use, including intravenous, intramuscular, intraperitoneal, or subcutaneous routes, the compounds of the disclosure may be provided in sterile aqueous solutions or suspensions, buffered to an appropriate pH and isotonicity or in parenterally acceptable oil. Suitable aqueous vehicles include Ringer's solution and isotonic sodium chloride. Such forms will be presented in unit-dose form such as ampules, auto-injectors, or disposable injection devices, in multi-dose forms such as vials from which the appropriate dose may be withdrawn, or in a solid form or pre-concentrate that can be used to prepare an injectable formulation. Illustrative infusion doses may range from about 1 to 1000 μg/kg/minute of compound, admixed with a pharmaceutical carrier over a period ranging from several minutes to several days. Other routes of administration include, without limitation, intracerebral, intraventricular, intracerebroventricular, intrathecal, intracisternal, intraspinal and/or peri-spinal routes.

For topical administration, the compounds may be mixed with a pharmaceutical carrier at a concentration of about 0.1% to about 10% of drug to vehicle. Another mode of administering the compounds of the disclosure may utilize a patch formulation to affect transdermal delivery.

Compounds of the disclosure may alternatively be administered in methods of this disclosure by inhalation, via the nasal or oral routes, e.g., in a spray formulation also containing a suitable carrier such as an aerosol or liquid spray.

Compound A, Form I, II, IIA, IIB, III, IV, V, or VI alone, or in combination with each other, are accordingly useful in inhibiting colony-stimulating factor-1 receptor. In some embodiments, Compound A, Form I, II, IIA, IIB, III, IV, V, or VI are useful in methods of treating a disease that is at least one of osteoporosis, Paget's disease, rheumatoid arthritis and other forms of inflammatory arthritis, osteoarthritis, prosthesis failure, osteolytic sarcoma, myeloma, or tumor metastasis to bone. In some embodiments, the disease is rheumatoid arthritis or cancer such as cancer metastasis to bone. In other embodiments, Compound A, Form I, II, IIA, IIB, III, IV, V, or VI are useful in treating a disease that is glomerulonephritis, inflammatory bowel disease, sarcoidosis, congestive obstructive pulmonary disease, idiopathic pulmonary fibrosis, asthma, pancreatitis, HIV infection, psoriasis, diabetes, tumor-related angiogenesis, age-related macular degeneration, diabetic retinopathy, restenosis, schizophrenia, or Alzheimer's dementia. In further embodiments, Compound A, Form I, II, IIA, IIB, III, IV, V, or VI is useful in treating pain, including skeletal pain caused by tumor metastasis or osteoarthritis, or visceral, inflammatory, or neurogenic pain. In still other embodiments, Compound A, Form I, II, IIA, IIB, III, IV, V, or VI is useful in treating a disease that is ovarian cancer, uterine cancer, breast cancer, prostate cancer, lung cancer, colon cancer, stomach cancer, or hairy cell leukemia. In yet further embodiments, Compound A, Form I, II, IIA, IIB, III, IV, V, or VI is useful in treating or preventing metastasis from ovarian cancer, uterine cancer, breast cancer, prostate cancer, lung cancer, colon cancer, stomach cancer, or hairy cell leukemia. In other embodiments, Compound A, Form I, II, IIA, IIB, III, IV, V, or VI is useful in treating an autoimmune disease that is at least one of systemic lupus erythematosus, rheumatoid arthritis and other forms of inflammatory arthritis, psoriasis, Sjogren's syndrome, multiple sclerosis, or uveitis.

The following Examples are set forth to aid in the understanding of the invention, and are not intended and should not be construed to limit in any way the invention set forth in the claims which follow thereafter.

EXAMPLES

X-ray powder diffraction (XRPD) was performed using an X-ray diffractometer (Philips Model X'Pert PRO PW3040) equipped with X'Celerator detector and graded multilayer parabolic X-ray mirror. The sample was scanned from 3 to 40° two theta at a step size of 0.0165° two theta and a time per step of 48.260 seconds. The x-ray tube voltage and current settings were 45 KV and 40 mA, respectively. The sample was packed on a zero background holder and scanned under ambient conditions of temperature and humidity.

One skilled in the art will recognize that diffraction patterns and peak positions are typically substantially independent of the diffractometer used and whether a specific calibration method is utilized. Typically, the peak positions may differ by about ±0.2° two theta, or less. The intensities (and relative intensities) of each specific diffraction peak may also vary as a function of various factors, including, but not limited to particle size, orientation, sample purity, etc. However the skilled person will be able to differentiate the between Compound A, Forms I, II, IIA, IIB, III, IV, V, and VI.

Thermal analyses were performed using a TA instrument Model Q1000 DSC. The sample was run in an open aluminum pan. The reference used was an empty aluminum pan. The sample was scanned from 25° to 300° C. with a programmed heating rate of 10° C./min. Total weight loss of the sample was obtained using a TA instrument Model Q5000 TGA. The sample was placed in a tarred aluminum pan, automatically weighed, and inserted into the TGA furnace. The sample was scanned from 25° to 300° C. at a heating rate of 10° C./min with a 25 mL/min nitrogen sample purge and a 10 mL/min nitrogen balance purge.

The moisture sorption analysis was performed using a Hiden Isochema system Model IGAsorp. The sample was run in a stainless-steel mesh crucible. The sample was initially dried at 60° C. for 30 minutes then the moisture profile was evaluated by monitoring vapor adsorption/desorption over the range of 0 to 90% relative humidity at 25° C. The moisture profile consisted of 2 cycles of vapor adsorption/desorption.

Example 1: Synthesis of Form I of Compound A

The hydrochloride salt of Compound A was prepared as described in U.S. Pat. No. 8,497,376. Water (150 mL) was added to the hydrochloride salt of Compound A (about 10 g). The formed solution was stirred using a stir plate. After several days, the solution was filtered using a Buchner glass filter under vacuum until the majority of the water was removed. A flow of $N_2$ gas was then applied onto the surface of the precipitate for about 1 hour to ensure complete removal of the solvent. The glass filter was weighed before and after the filtration and the net weight was recorded.

A portion of the precipitate was analyzed using XRD and the results confirmed the conversion of the salt to the free base, Form I of Compound A. The glass filter was placed in a vacuum oven at 60° C. overnight to ensure complete dryness until a constant weight was obtained. The isolated solid (Form I of Compound A, as a freebase) was characterized using XRPD, DSC, TGA, and DVS.

Figure 12:
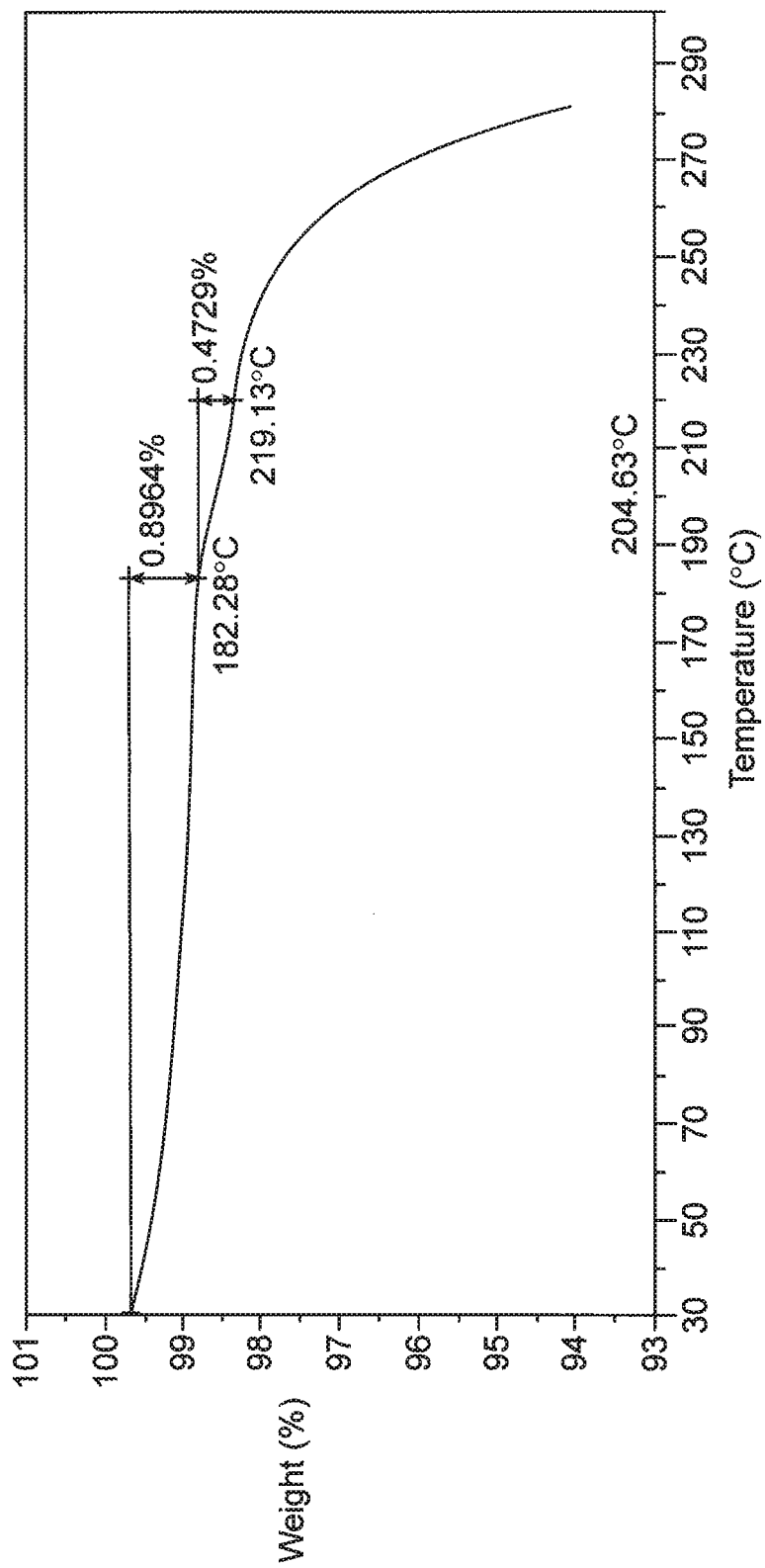
FIG. 12 is a thermogravimetric analysis (TGA) spectrum of Compound A, Form I, prepared by slurrying the HCl salt of Compound A with water.
Figure 15:
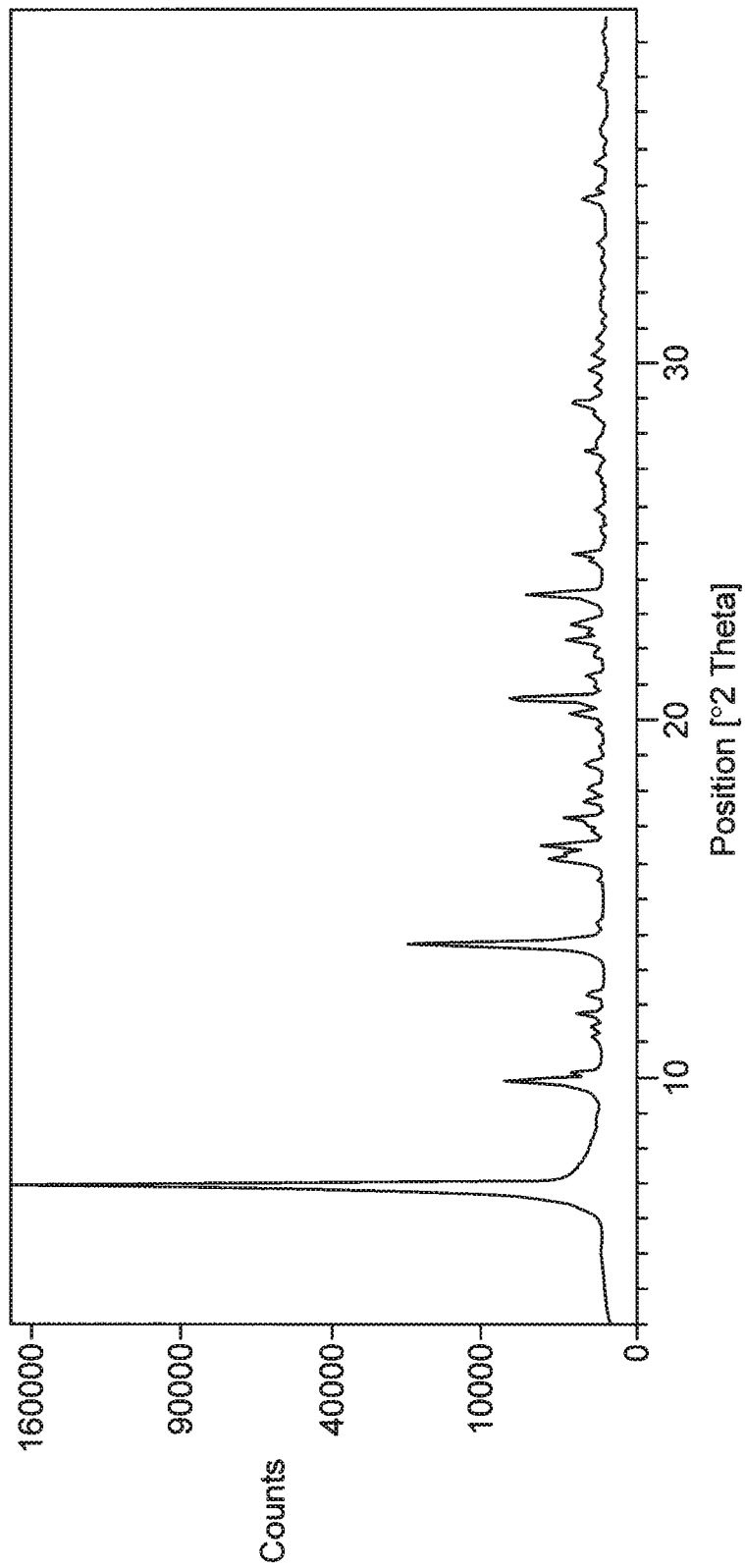
FIG. 15 is an XRPD pattern of the HCl salt of Compound A.
Figure 16:
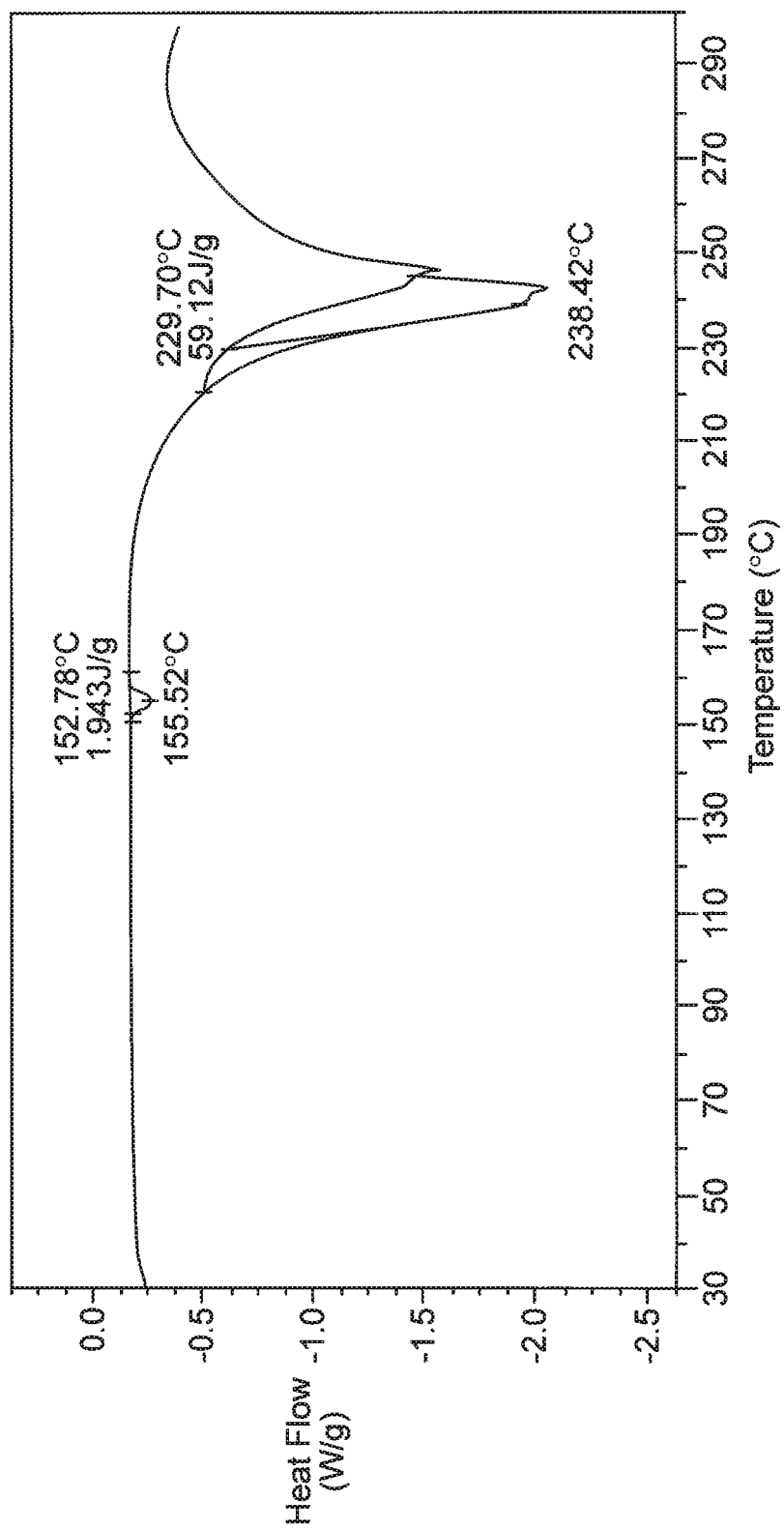
FIG. 16 is a DSC thermogram of the HCl salt of Compound A.
Figure 17:
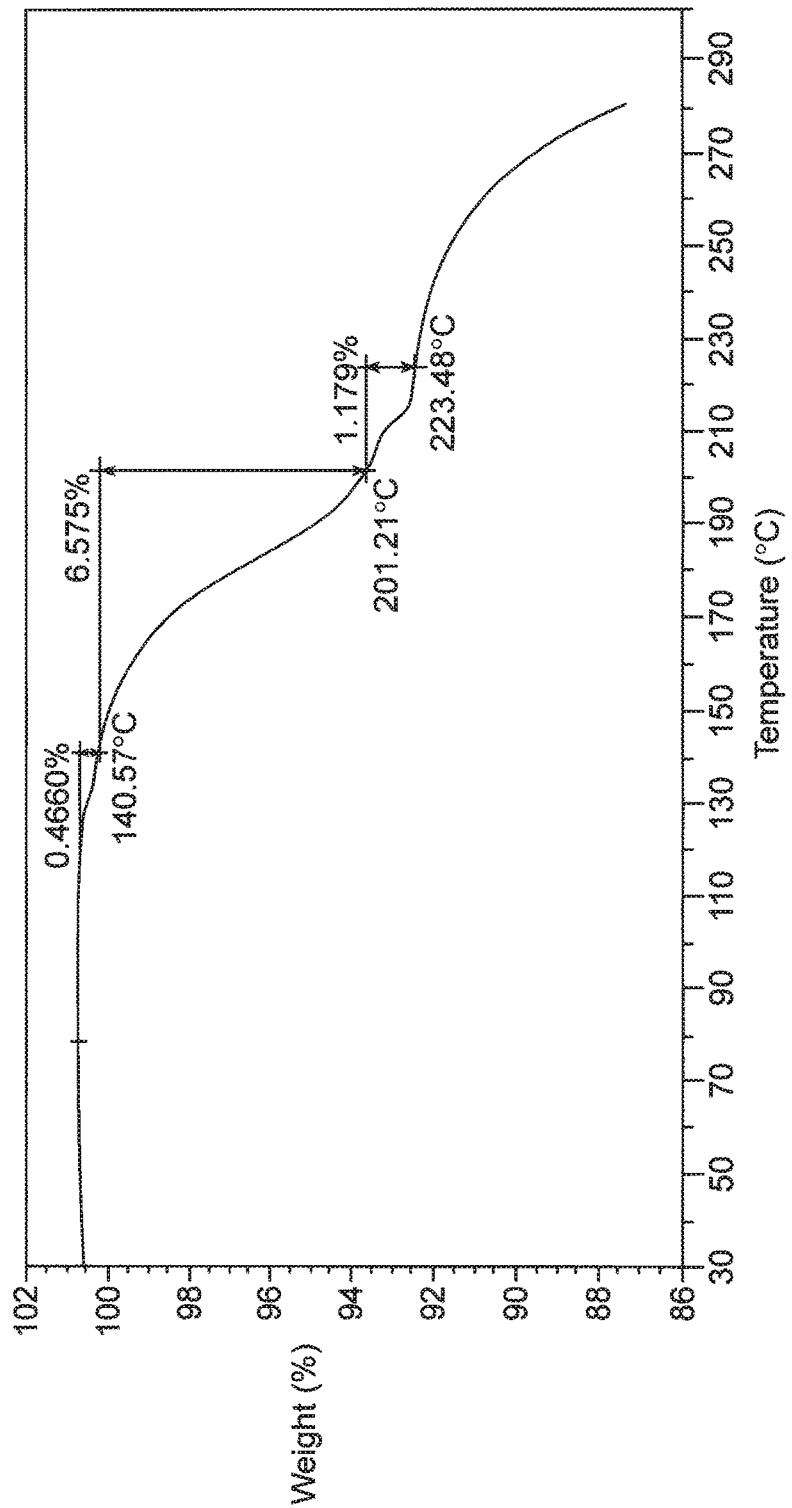
FIG. 17 is a TGA spectrum of the HCl salt of Compound A.

The isolated solid (Compound A, as a freebase) was a white crystalline solid, hygroscopic and insoluble in water as determined by USP methods. The isolated solid displayed an XRPD spectrum consistent with Compound A, Form I, having sharp and intense reflections indicating a crystalline form (as shown in FIG. 10). The XRD for Form I of Compound A differed from the XRD of a sample of the HCl salt of Compound A (e.g., FIG. 15). The DSC spectrum of the isolated solid (Compound A, Form I) showed a broad endothermic peak up to 110° C. due to surface water loss followed by melting with onset and peak temperatures at 187.5° C. and 204.6° C., respectively, and a heat of fusion of 56.2 J/g (as shown in FIG. 11). This also differed from the DSC spectrum of the HCl salt of Compound A as shown in FIG. 16. Thermogravimetric analysis of the isolated solid (Compound A, Form I) showed a two-step weight loss of 0.9% between room temperature (RT, about 20° C.) and 182° C. (equivalent to 0.23 mole of water) due to surface water loss and 0.5% between 182° C. and 219° C. due to melting/decomposition (as shown in FIG. 12). This differed from the TGA spectrum of the HCl salt of Compound A (e.g., FIG. 17).

Figure 13:
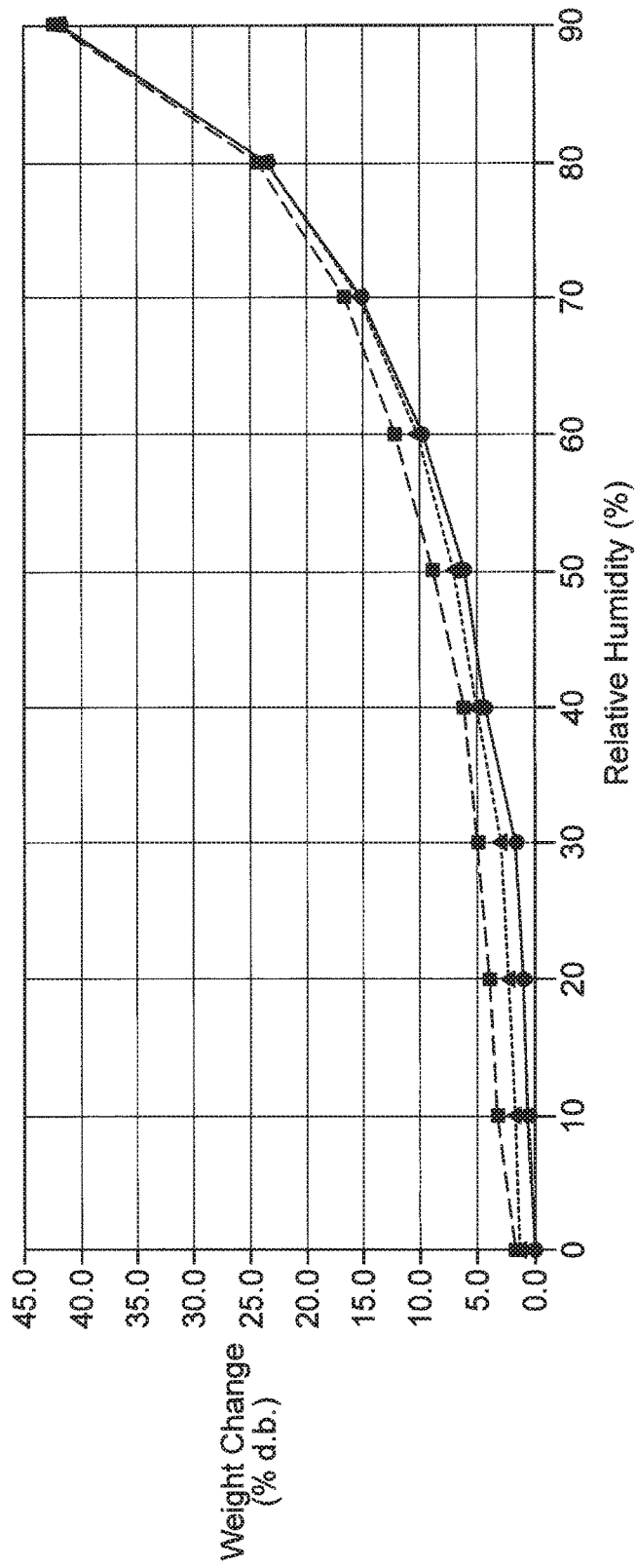
FIG. 13 is a dynamic vapor sorption (DVS) spectrum of Compound A, Form I, prepared by slurrying the HCl salt of Compound A with water, showing two cycles of adsorption/desorption.
Figure 14:
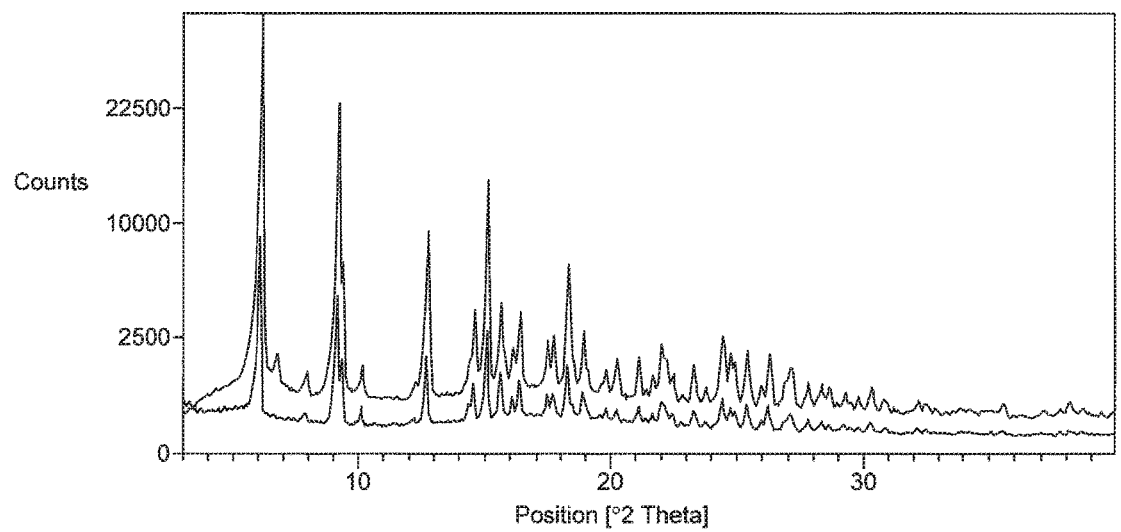
FIG. 14 illustrates a comparison of the XRPD pattern of a representative sample of the Compound A, Form I before DVS (lower pattern) and the XRPD of a representative sample of the material isolated after DVS (upper pattern); also exhibiting a pattern consistent with Compound A, Form I.
Figure 18:
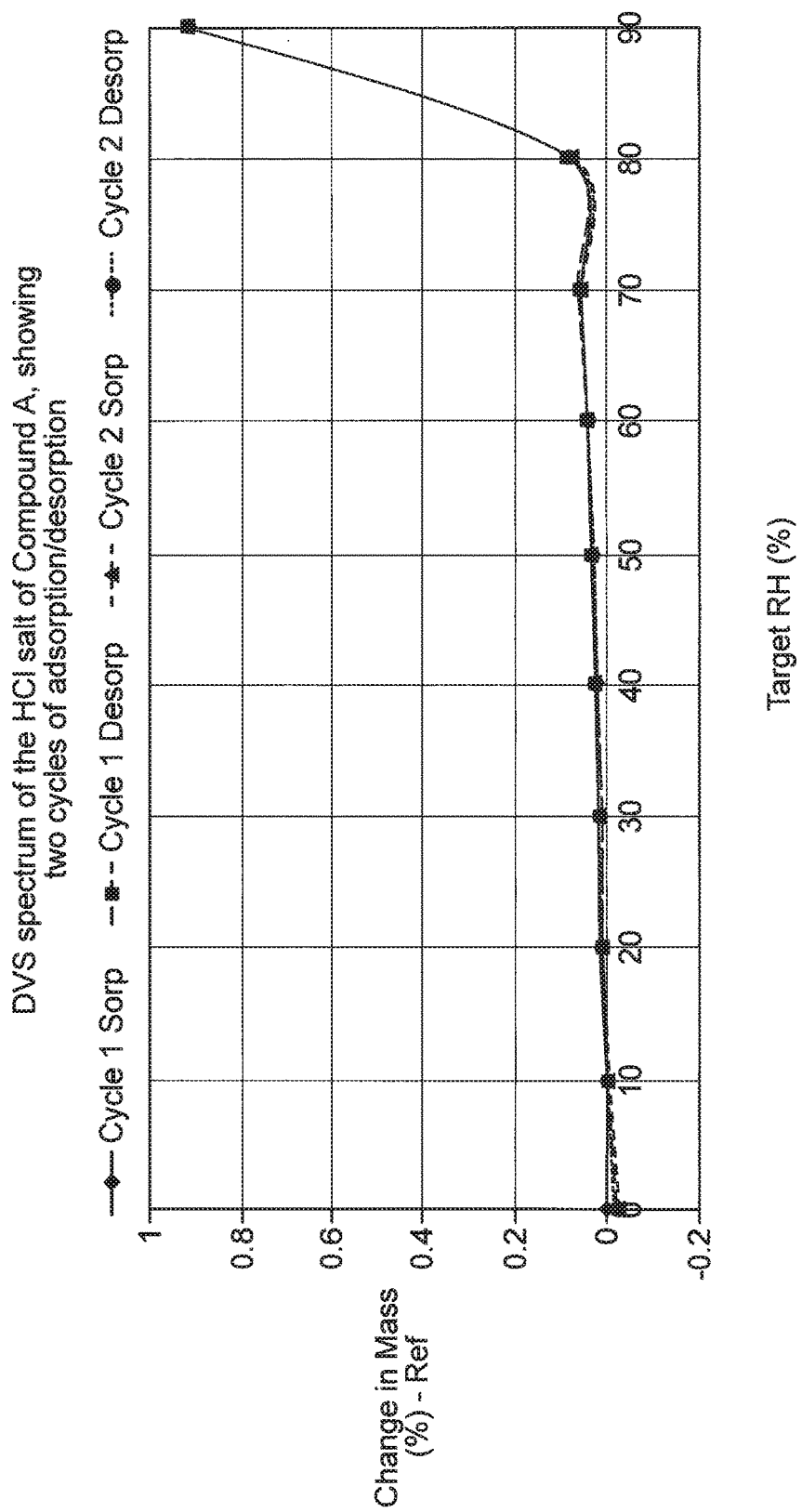
FIG. 18 is a DVS spectrum of the HCl salt of Compound A, showing two cycles of adsorption/desorption.

DVS of the isolated solid (Compound A, Form I) showed that it was hygroscopic with moisture adsorption of 41.8% up to 90% RH. The isolated solid (Compound A, Form I) also showed little hysteresis and retained 1.8% moisture (equivalent to 0.47 mole of water, hemihydrate form) at the end of a second moisture sorption-desorption cycle (as shown in FIG. 13). A comparison of XRPD analysis of the isolated solid (before DVS) and the solid residue after DVS showed a substantially similar diffraction pattern, with only a single extra peak at 6.7 2θ (FIG. 14), indicating that the crystalline form did not change upon humidity cycling. The DVS spectra differed from the DVS for the HCl salt of Compound A as shown in FIG. 18.

Example 2: Synthesis of Forms II, IIA, IIB, III, IV, V, and VI of Compound A

An automated solid-state form screening of Compound A was done using a binary solvent system. Screening experiments consisted of an array of 13 solvents (water, methanol, ethanol, acetone, acetonitrile, isopropyl alcohol, ethyl acetate, toluene, tetrahydrofuran (THF), dichloromethane, 2-butanone (MEK), 1-butanol, and heptane) under slow evaporation crystallization conditions. Specifically, saturated solutions of Compound A (prepared as described in Example 1 above) in 13 different solvents were prepared by adding solid powder of Compound A, Form I (50 mg, prepared as described in Example 1 above) and the selected solvent to 20 mL vials. The resulting solutions were stirred and heated to 40° C. All preparations dissolved quickly except in water, toluene, and heptane. Table 1 provides a summary of the visual solubility of Compound A, Form I in the noted solvents.

TABLE 1

| Solvent Systems | Solvent Volume (mL) | Solubility (mg/mL) | Visual Solubility |
| --- | --- | --- | --- |
| Water | 10 | n/a | Suspension |
| Methanol | 10 | >5 | Dissolve |
| Ethanol | 10 | >5 | Dissolve |
| Acetone | 10 | >5 | Dissolve |
| Acetonitrile | 10 | >5 | Dissolve |
| IPA | 10 | >5 | Dissolve |
| Ethyl Acetate | 10 | >5 | Dissolve |
| Toluene | 10 | n/a | Suspension |
| THF | 10 | >5 | Dissolve |
| Dichloromethane | 10 | >5 | Dissolve |
| MethylEthylKetone (MEK) | 10 | >5 | Dissolve |
| Heptane | 10 | n/a | Suspension |
| 1-Butanol | 10 | >5 | Dissolve |

The solutions were then filtered through a 0.2 μm PTFE filter cartridge and dispensed into 91 wells of a 96 well, 1 mL glass vial plate for a total volume of 900 μL (50:50) using a Gilson Liquid Handling System, and allowed to sit covered overnight under ambient conditions. The cover was removed the following day and the solution allowed to evaporate overnight. After evaporation, all the solid residues were characterized using X-ray Powder Diffraction (XRPD), Differential Scanning calorimetry (DSC) and Thermogravimetric Analysis (TGA).

Table 2 provides a summary of the contents of each of the 91 wells (5 wells were empty) and the crystalline form of Compound A of each isolated residue.

TABLE 2

| # | Solvent 1 | Solvent 2 | Isolated Residue Crystalline Form |
| --- | --- | --- | --- |
| 1 | Water | Water | NA |
| 2 | Water | Methanol | I |
| 3 | Water | Ethanol | I |
| 4 | Water | Acetone | I |
| 5 | Water | Acetonitrile | I |
| 6 | Water | IPA | I |
| 7 | Water | Ethyl Acetate | IV |
| 8 | Water | Toluene | IIB |
| 9 | Water | THF | II |
| 10 | Water | Dichloromethane | I |
| 11 | Water | MEK | II |
| 12 | Water | 1-Butanol | I |
| 13 | Water | Heptane | NA |
| 14 | Methanol | Methanol | III |
| 15 | Methanol | Ethanol | II |
| 16 | Methanol | Acetone | II |
| 17 | Methanol | Acetonitrile | III |
| 18 | Methanol | IPA | III |
| 19 | Methanol | Ethyl Acetate | IV |
| 20 | Methanol | Toluene | IIA |
| 21 | Methanol | THF | IV |
| 22 | Methanol | Dichloromethane | I |
| 23 | Methanol | MEK | II |
| 24 | Methanol | 1-Butanol | I |
| 25 | Methanol | Heptane | III |
| 26 | Ethanol | Ethanol | PC |
| 27 | Ethanol | Acetone | II |
| 28 | Ethanol | Acetonitrile | III |
| 29 | Ethanol | IPA | I |
| 30 | Ethanol | Ethyl Acetate | III |
| 31 | Ethanol | Toluene | III |
| 32 | Ethanol | THF | III |
| 33 | Ethanol | Dichloromethane | I |
| 34 | Ethanol | MEK | II |
| 35 | Ethanol | 1-Butanol | I |
| 36 | Ethanol | Heptane | IIA |
| 37 | Acetone | Acetone | IIA |
| 38 | Acetone | Acetonitrile | IIA |
| 39 | Acetone | IPA | II |
| 40 | Acetone | Ethyl Acetate | II |
| 41 | Acetone | Toluene | IIA |
| 42 | Acetone | THF | IIA |
| 43 | Acetone | Dichloromethane | II |
| 44 | Acetone | MEK | II |
| 45 | Acetone | 1-Butanol | IIA |
| 46 | Acetone | Heptane | IIA |
| 47 | Acetonitrile | Acetonitrile | II |
| 48 | Acetonitrile | IPA | IIA |
| 49 | Acetonitrile | Ethyl Acetate | II |
| 50 | Acetonitrile | Toluene | IIB |
| 51 | Acetonitrile | THF | IIA |
| 52 | Acetonitrile | Dichloromethane | IIB |
| 53 | Acetonitrile | MEK | II |
| 54 | Acetonitrile | 1-Butanol | I |
| 55 | Acetonitrile | Heptane | II |
| 56 | IPA | IPA | V |
| 57 | IPA | Ethyl Acetate | II |
| 58 | IPA | Toluene | II |
| 59 | IPA | THF | II |
| 60 | IPA | Dichloromethane | V |
| 61 | IPA | MEK | II |
| 62 | IPA | 1-Butanol | I |
| 63 | IPA | Heptane | IV |
| 64 | Ethyl Acetate | Ethyl Acetate | II |
| 65 | Ethyl Acetate | Toluene | II |
| 66 | Ethyl Acetate | THF | II |
| 67 | Ethyl Acetate | Dichloromethane | IV |
| 68 | Ethyl Acetate | MEK | II |
| 69 | Ethyl Acetate | 1-Butanol | I |
| 70 | Ethyl Acetate | Heptane | IIB |
| 71 | Toluene | Toluene | IIB |
| 72 | Toluene | THF | IIB |
| 73 | Toluene | Dichloromethane | IIB |
| 74 | Toluene | MEK | II |
| 75 | Toluene | 1-Butanol | II |
| 76 | Toluene | Heptane | II |
| 77 | THF | THF | II |
| 78 | THF | Dichloromethane | II |
| 79 | THF | MEK | II |
| 80 | THF | 1-Butanol | I |
| 81 | THF | Heptane | IIB |
| 82 | Dichloromethane | Dichloromethane | II |
| 83 | Dichloromethane | MEK | II |
| 84 | Dichloromethane | 1-Butanol | I |
| 85 | Dichloromethane | Heptane | IIB |

TABLE 2-continued

| # | Solvent 1 | Solvent 2 | Isolated Residue Crystalline Form |
|---|---|---|---|
| 86 | MEK | MEK | VI |
| 87 | MEK | 1-Butanol | I |
| 88 | MEK | Heptane | IIA |
| 89 | 1-Butanol | 1-Butanol | NA |
| 90 | 1-Butanol | Heptane | NA |
| 91 | Heptane | Heptane | NA |

NA = not applicable;
PC = partially crystalline

Table 3A provides the peak listings for the XRPD of Compound A, Form I (see also, FIG. 1).

TABLE 3A

| Position [°2θ] | Relative Intensity [%] |
|---|---|
| 6.1 | 100.0 |
| 9.2 | 53.6 |
| 9.4 | 16.5 |
| 10.2 | 2.0 |
| 12.7 | 18.4 |
| 14.6 | 7.8 |
| 15.1 | 28.0 |
| 15.7 | 10.4 |
| 16.2 | 4.1 |
| 16.4 | 8.5 |
| 17.6 | 4.8 |
| 17.8 | 4.9 |
| 18.4 | 13.4 |
| 19.0 | 5.4 |
| 19.9 | 2.1 |
| 20.3 | 2.6 |
| 21.2 | 2.4 |
| 22.0 | 3.4 |
| 24.5 | 5.1 |
| 25.0 | 2.1 |
| 25.4 | 3.2 |
| 26.3 | 3.0 |
| 27.2 | 2.1 |

Table 3B provides the peak listings for the XRPD of Compound A, Form II (see, also, FIG. 2).

TABLE 3B

| Position [°2θ] | Relative Intensity [%] |
|---|---|
| 6.3 | 100.0 |
| 7.3 | 5.9 |
| 11.5 | 6.0 |
| 12.6 | 3.0 |
| 14.0 | 2.5 |
| 14.6 | 2.3 |
| 17.0 | 12.4 |
| 18.3 | 5.6 |
| 18.8 | 3.9 |
| 22.1 | 2.2 |
| 23.0 | 4.7 |
| 28.5 | 2.7 |

Table 3C provides the peak listings for the XRPD of Compound A, Form IIA (see, also, FIG. 3).

TABLE 3C

| Position [°2θ] | Relative Intensity [%] |
|---|---|
| 5.7 | 5.0 |
| 5.9 | 9.8 |
| 6.4 | 100.0 |
| 7.3 | 7.6 |
| 7.4 | 6.7 |

TABLE 3C-continued

| Position [°2θ] | Relative Intensity [%] |
|---|---|
| 11.5 | 7.2 |
| 12.6 | 3.0 |
| 14.1 | 10.2 |
| 14.6 | 7.7 |
| 17.1 | 31.6 |
| 18.3 | 10.9 |
| 18.9 | 14.6 |
| 19.3 | 7.6 |
| 20.2 | 3.3 |
| 22.1 | 3.0 |
| 23.0 | 19.8 |
| 25.3 | 3.5 |
| 29.3 | 4.2 |

Table 3D provides the peak listings for the XRPD of Compound A, Form IIB (see, also, FIG. 4).

TABLE 3D

| Position [°2θ] | Relative Intensity [%] |
|---|---|
| 6.3 | 100.0 |
| 12.6 | 3.2 |
| 14.0 | 1.5 |
| 18.9 | 8.6 |
| 25.2 | 1.8 |

Table 3E provides the peak listings for the XRPD of Compound A, Form III (see, also, FIG. 5).

TABLE 3E

| Position [°2θ] | Relative Intensity [%] |
|---|---|
| 4.6 | 22.1 |
| 6.3 | 100.0 |
| 6.8 | 23.2 |
| 7.4 | 7.7 |
| 9.1 | 19.4 |
| 11.7 | 8.0 |
| 12.6 | 9.1 |
| 17.1 | 15.0 |
| 18.1 | 6.1 |
| 19.4 | 3.7 |
| 23.0 | 8.7 |
| 28.5 | 15.9 |

Table 3F provides the peak listings for the XRPD of Compound A, Form IV (see, also, FIG. 6).

TABLE 3F

| Position [°2θ] | Relative Intensity [%] |
|---|---|
| 3.5 | 3.1 |
| 6.3 | 100.0 |
| 6.6 | 29.1 |
| 6.9 | 44.0 |
| 7.3 | 10.1 |
| 11.7 | 8.0 |
| 12.6 | 2.3 |
| 13.2 | 2.5 |
| 13.7 | 2.5 |
| 14.1 | 2.5 |
| 14.6 | 3.6 |
| 17.1 | 12.1 |
| 18.3 | 7.4 |
| 18.9 | 3.7 |
| 20.2 | 3.7 |
| 20.7 | 2.2 |
| 22.0 | 2.5 |
| 23.0 | 5.4 |

Table 3G provides the peak listings for the XRPD of Compound A, Form V (see, also, FIG. 7).

TABLE 3G

| Position [°2θ] | Relative Intensity [%] |
| --- | --- |
| 5.3 | 5.0 |
| 6.3 | 100.0 |
| 7.4 | 13.5 |
| 11.5 | 8.0 |
| 11.7 | 8.7 |
| 12.6 | 3.5 |
| 13.3 | 3.0 |
| 14.0 | 3.3 |
| 14.7 | 4.6 |
| 17.0 | 17.6 |
| 18.3 | 9.7 |
| 18.9 | 4.2 |
| 19.2 | 2.7 |
| 20.2 | 5.5 |
| 22.1 | 3.2 |
| 23.0 | 7.3 |

Table 3H provides the peak listings for the XRPD of Compound A, Form VI (see, also, FIG. 8).

TABLE 3H

| Position [°2θ] | Relative Intensity [%] |
| --- | --- |
| 5.7 | 100.0 |
| 6.3 | 1.9 |
| 6.7 | 3.5 |
| 7.3 | 7.7 |
| 8.8 | 4.1 |
| 10.8 | 11.8 |
| 11.4 | 17.4 |
| 13.2 | 8.1 |
| 14.0 | 6.6 |
| 15.4 | 3.0 |
| 15.7 | 5.2 |
| 16.1 | 2.4 |
| 17.1 | 13.5 |
| 17.5 | 2.1 |
| 18.0 | 4.9 |
| 18.4 | 2.2 |
| 19.2 | 8.8 |
| 20.8 | 2.4 |
| 24.7 | 2.3 |
| 25.5 | 1.9 |

Example 3: Slurry Studies

Small scale saturated solutions of Compound A, Form I (prepared as described in Example 1 above) in the organic solvents noted in Example 2, except water, toluene, or heptane, were prepared as follows. Compound A, Form I (5-10 mg) was added to 2 mL HPLC vials and the selected solvent (50 μL) was added. The resulting slurries were stirred at 300 rpm for up to 1 day. At 1 hour and 1 day time-points, a sample of each slurry was placed on an XRPD sample holder and the solvent evaporated under ambient conditions to yield a solid residue which was then analyzed by X-ray powder diffraction. Table 4 provides the slurry conditions and the crystalline form isolated, as determined by XRPD.

TABLE 4

| Slurry Systems | Saturated Conc. (mg/mL) | XRPD Form @ 1 Hr & 1 Day |
| --- | --- | --- |
| Methanol | 80 | I |
| Ethanol | 110 | I |

TABLE 4-continued

| Slurry Systems | Saturated Conc. (mg/mL) | XRPD Form @ 1 Hr & 1 Day |
| --- | --- | --- |
| Acetone | 130 | I |
| Acetonitrile | 80 | I |
| IPA (isopropyl acetate) | 95 | I |
| Ethyl Acetate | 120 | I |
| THF (tetrahydrofuran) | 420 | II |
| DCM (dichloromethane) | 210 | III |
| 1-Butanol | 90 | I |

These results show that the powder X-ray analyses of solids isolated from all solvent slurries except THF and DCM exhibit an XRPD pattern consistent with Form I. The results show that the crystalline form did not change after 1 hour suspended in all solvents except THF and DCM, as indicated by XRPD. The XRPD analysis of the solid residues from slurry in THF showed a pattern similar to Form II and this pattern did not change after 1 day. The XRPD of the solid residue from dichloromethane showed a pattern that was not similar to any of the free base form, and this did not change after 1 day.

Example 4

Competitive slurry studies of Compound A, Forms II, IIA, IIB, III, IV, V, and VI were conducted at RT (room temperature, about 20° C.) and 50° C. in water. The slurry at room temperature was monitored using XRPD over time (where the slurry was sampled at selected time points, the sample placed on an XRPD sample holder, the solvent allowed to evaporate under ambient conditions to yield a residue, and an XRPD measured for the residue) and complete conversion to Form I was observed to occur after 3 days. A small portion of the slurry was transferred to 50° C. after 2 days and analyzed using powder X-ray after being slurred at 50° C. for 2 hours (where a sample of the slurry was placed on an XRPD sample holder, the solvent allowed to evaporate under ambient conditions to yield a residue, and an XRPD measured for the residue). Complete conversion to Form I took place within 2 hours of heating.

Based on the above results, Form I is hypothesized to be the most thermodynamically stable polymorph as indicated by competitive slurry.

The disclosures of each patent, patent application, and publication cited or described in this document are hereby incorporated herein by reference, in its entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed is:

1. A crystalline form of 4-cyano-N-[2-(4,4-dimethylcyclohex-1-en-1-yl)-6-(2,2,6,6-tetramethyltetrahydro-2H-pyran-4-yl)pyridine-3-yl]-1H-imidazole-2-carboxamide (Compound A)

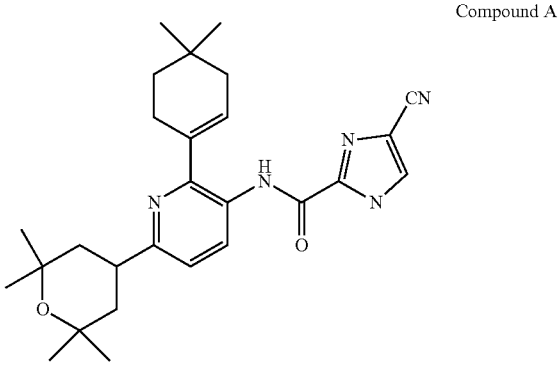 [SMILES: CC1(C)CC=C(c2nc(C3CC(C)(C)OC(C)(C)C3)ccc2NC(=O)c2nc(C#N)c[nH]2)CC1]

Compound A wherein the crystalline form is selected from the group consisting of Compound A, Form I, producing an X-ray powder diffraction pattern comprising peaks at 6.1, 9.2, 9.4, 12.7, 15.1, 15.7, and 18.4 degrees two theta±0.2 degrees two theta;

Compound A, Form II, producing an X-ray powder diffraction pattern comprising peaks at 6.3, 7.3, 11.5, 17.0 and 18.3 degrees two theta±0.2 degrees two theta;

Compound A, Form IIA, producing an X-ray powder diffraction pattern comprising peaks at 6.4, 14.1, 14.6, 17.1, 18.3, 18.9, 19.3 and 23.0 degrees two theta±0.2 degrees two theta;

Compound A, Form IIB, producing an X-ray powder diffraction pattern comprising peaks at 6.3 and 18.9 degrees two theta±0.2 degrees two theta;

Compound A, Form III, producing an X-ray powder diffraction pattern comprising peaks at 4.6, 6.3, 6.8, 9.1, 17.1, and 28.5 degrees two theta±0.2 degrees two theta;

Compound A, Form IV, producing an X-ray powder diffraction pattern comprising peaks at 6.3, 6.6, 6.9, 7.3, 11.7, 17.1 and 18.3 degrees two theta±0.2 degrees two theta;

Compound A, Form V, producing an X-ray powder diffraction pattern comprising peaks at 6.3, 7.4, 11.5, 11.7, 17.0, 18.3 and 23.0 degrees two theta±0.2 degrees two theta; and Compound A, Form VI, producing an X-ray powder diffraction pattern comprising peaks at 5.7, 10.8, 11.4 and 17.1 degrees two theta±0.2 degrees two theta.

2. The crystalline form of claim 1 that is Compound A, Form I.

3. The crystalline form of claim 2 that is Compound A, Form I, wherein the X-ray powder diffraction pattern further comprises one or more peaks at 14.6, 16.4, or 19.0 degrees two theta±0.2 degrees two theta.

4. The crystalline form of claim 1 that is Compound A, Form I, further characterized by a differential scanning calorimetry thermogram comprising an endotherm with a peak temperature at about 204.6° C.

5. The crystalline form of claim 1 that is Compound A, Form I, further characterized by an X-ray powder diffraction pattern substantially as depicted in FIG. 1.

6. The crystalline form of claim 1 that is Compound A, Form II.

7. The crystalline form of claim 6 that is Compound A, Form II, wherein the X-ray powder diffraction pattern further comprises one or more peaks at 14.0, 14.6, 18.8 or 23.0 degrees two theta±0.2 degrees two theta.

8. The crystalline form of claim 1 that is Compound A, Form II, further characterized by an X-ray powder diffraction pattern substantially as depicted in FIG. 2.

9. The crystalline form of claim 1 that is Compound A, Form II further characterized by a differential scanning calorimetry thermogram comprising an endotherm with a peak temperature at about 199.1° C.

10. The crystalline form of claim 1 that is Compound A, Form IIA.

11. The crystalline form of claim 10 that is Compound A, Form IIA, wherein the X-ray powder diffraction pattern further comprises one or more peaks at 5.9, 7.3, 7.4, 11.5, 12.6, 18.3, 18.9, 20.2, 25.3, or 29.3 degrees two theta±0.2 degrees two theta.

12. The crystalline form of claim 1 that is Compound A, Form IIA, further characterized by an X-ray powder diffraction pattern substantially as depicted in FIG. 3.

13. The crystalline form of claim 1 that is Compound A, Form IIB.

14. The crystalline form of claim 13 that is Compound A, Form IIB, wherein the X-ray powder diffraction pattern further comprises one or more peaks at 12.6, 14.0 or 25.2 degrees two theta±0.2 degrees two theta.

15. The crystalline form of claim 1 that is Compound A, Form IIB, further characterized by an X-ray powder diffraction pattern substantially as depicted in FIG. 4.

16. The crystalline form of claim 1 that is Compound A, Form III.

17. The crystalline form of claim 16 that is Compound A, Form III, wherein the X-ray powder diffraction pattern further comprises one or more peaks at 7.4, 11.7, 12.6, 18.1 or 23.0 degrees two theta±0.2 degrees two theta.

18. The crystalline form of claim 1 that is Compound A, Form III, further characterized by an X-ray powder diffraction pattern substantially as depicted in FIG. 5.

19. The crystalline form of claim 1 that is Compound A, Form III, further characterized by a differential scanning calorimetry thermogram comprising an endotherm with a peak temperature at about 182.9° C.

20. The crystalline form of claim 1 that is Compound A, Form IV.

21. The crystalline form of claim 20 that is Compound A, Form IV, wherein the X-ray powder diffraction pattern further comprises one or more peaks at 3.5, 14.6, 18.9, 20.2, or 23.0 degrees two theta±0.2 degrees two theta.

22. The crystalline form of claim 1 that is Compound A, Form IV, further characterized by an X-ray powder diffraction pattern substantially as depicted in FIG. 6.

23. The crystalline form of claim 1 that is Compound A, Form IV, further characterized by a differential scanning calorimetry thermogram comprising an endotherm with a peak temperature at about 207.5° C.

24. The crystalline form of claim 1 that is Compound A, Form V.

25. The crystalline form of claim 24 that is Compound A, Form V, wherein the X-ray powder diffraction pattern further comprises one or more peaks at 5.3, 12.6, 13.3, 14.0, 14.7, 18.3, 19.2, 20.2 or 22.1 degrees two theta±0.2 degrees two theta.

26. The crystalline form of claim 1 that is Compound A, Form V, further characterized by an X-ray powder diffraction pattern substantially as depicted in FIG. 7.

27. The crystalline form of claim 1 that is Compound A, Form V, further characterized by a differential scanning calorimetry thermogram comprising an endotherm with a peak temperature at about 188.6° C.

28. The crystalline form of claim 1 that is Compound A, Form VI.

29. The crystalline form of claim 28 that is Compound A, Form VI, wherein the X-ray powder diffraction pattern further comprises one or more peaks at 7.3, 13.2, 14.0, 15.7, 18.0 or 19.2 degrees two theta±0.2 degrees two theta.

30. The crystalline form of claim 1 that is Compound A, Form VI, further characterized by an X-ray powder diffraction pattern substantially as depicted in FIG. 8.

31. A pharmaceutical composition comprising the crystalline form of claim 1 and at least one pharmaceutically acceptable excipient.

32. A method of inhibiting colony-stimulating factor-1 receptor in a subject, said method comprising administered at least one crystalline form of claim 1 to said subject.

33. A method of treating a disease that is at least one of osteoporosis, Paget's disease, rheumatoid arthritis, osteoarthritis, prosthesis failure, ovarian cancer, uterine cancer, breast cancer, prostate cancer, lung cancer, colon cancer, stomach cancer, hairy cell leukemia, osteolytic sarcoma, myeloma, or tumor metastasis to bone of ovarian cancer, uterine cancer, breast cancer, prostate cancer, lung cancer, colon cancer, stomach cancer, or hairy cell leukemia, in a subject comprising administering a therapeutically effective amount of at least one crystalline form of claim 1 to said subject.

34. The method of claim 33, wherein said disease is rheumatoid arthritis, ovarian cancer, uterine cancer, breast cancer, prostate cancer, lung cancer, colon cancer, stomach cancer, hairy cell leukemia, osteolytic sarcoma, or myeloma.

35. The method of claim 33, wherein said disease is tumor metastasis to bone of ovarian cancer, uterine cancer, breast cancer, prostate cancer, lung cancer, colon cancer, stomach cancer, or hairy cell leukemia.

36. A method of treating a disease that is at least one of glomerulonephritis, inflammatory bowel disease, sarcoidosis, congestive obstructive pulmonary disease, idiopathic pulmonary fibrosis, asthma, pancreatitis, HIV infection, psoriasis, tumor-related angiogenesis, age-related macular degeneration, diabetic retinopathy, restenosis, or schizophrenia in a subject comprising administering a therapeutically effective amount of at least one crystalline form of claim 1 to the subject.

37. A method of treating pain in a subject comprising administering to the subject a therapeutically effective amount of at least one crystalline form of claim 1 to the subject.

38. The method of claim 34, wherein said disease is ovarian cancer, uterine cancer, breast cancer, prostate cancer, lung cancer, colon cancer, stomach cancer, or hairy cell leukemia.

39. A method of treating an autoimmune disease that is at least one of systemic lupus erythematosus, rheumatoid arthritis psoriasis, Sjogren's syndrome, multiple sclerosis, or uveitis in a subject comprising administering a therapeutically effective amount of at least one crystalline form of claim 1 to the subject.

40. The method of claim 37 wherein the pain is selected from the group consisting of skeletal pain caused by tumor metastasis, osteoarthritis, or visceral, inflammatory, and neurogenic pain.

41. The method of claim 34 wherein said disease is osteolytic sarcoma or myeloma.

* * * * *

UNITED STATES PATENT AND TRADEMARK OFFICE
CERTIFICATE OF CORRECTION

PATENT NO. : 10,314,821 B2
APPLICATION NO. : 15/651385
DATED : June 11, 2019
INVENTOR(S) : Fawzy et al.

Page 1 of 1

It is certified that error appears in the above-identified patent and that said Letters Patent is hereby corrected as shown below:

In Claim 33, Column 19, Line 21: Replace "myeloma," with -- myeloma; --.

Signed and Sealed this
Sixth Day of August, 2019

Andrei Iancu
*Director of the United States Patent and Trademark Office*